(12) United States Patent
Awiszus et al.

(10) Patent No.: US 9,998,804 B2
(45) Date of Patent: Jun. 12, 2018

(54) PERSONAL PROTECTIVE EQUIPMENT (PPE) WITH ANALYTICAL STREAM PROCESSING FOR SAFETY EVENT DETECTION

(71) Applicant: 3M INNOVATIVE PROPERTIES COMPANY, St. Paul, MN (US)

(72) Inventors: Steven T. Awiszus, Woodbury, MN (US); Eric C. Lobner, Woodbury, MN (US); Michael G. Wurm, Waukesha, WI (US); Kiran S. Kanukurthy, Cottage Grove, MN (US); Jia Hu, Mounds View, MN (US); Matthew J. Blackford, Hastings, MN (US); Keith G. Mattson, Woodbury, MN (US); Ronald D. Jesme, Plymouth, MN (US); Nathan J. Anderson, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days. days.

(21) Appl. No.: 15/631,870

(22) Filed: Jun. 23, 2017

(65) Prior Publication Data
US 2017/0374436 A1 Dec. 28, 2017

Related U.S. Application Data

(63) Continuation-in-part of application No. 15/190,564, filed on Jun. 23, 2016.
(Continued)

(51) Int. Cl.
*G06F 17/30* (2006.01)
*H04Q 9/00* (2006.01)
(Continued)

(52) U.S. Cl.
CPC .............. *H04Q 9/00* (2013.01); *A61F 9/06* (2013.01); *A62B 9/00* (2013.01); *A62B 18/00* (2013.01);
(Continued)

(58) Field of Classification Search
CPC ...................... H04Q 9/00; G06F 17/30516
See application file for complete search history.

(56) References Cited

U.S. PATENT DOCUMENTS 4,619,255 A 10/1986 Spinosa et al.
5,189,735 A 3/1993 Corona
(Continued)

FOREIGN PATENT DOCUMENTS

DE 10 2015 001 513 3/2016
GB 2409961 7/2005
(Continued)

OTHER PUBLICATIONS

Sandulescu, "Wearable System for Stress Monitoring of Firefighters in Special Missions", The 5th IEEE International Conference on E-Health and Bioengineering—EHB 2015, Nov. 19-21, 2015, pp. 1-4.
(Continued)

*Primary Examiner* — Nay Tun
(74) *Attorney, Agent, or Firm* — Christopher D. Karlen

(57) ABSTRACT

In some examples, a system includes an article of personal protective equipment (PPE) having at least one sensor configured to generate a stream of usage data; and an analytical stream processing component comprising: a communication component that receives the stream of usage data; a memory configured to store at least a portion of the stream of usage data and at least one model for detecting a safety event signature, wherein the at least one model is trained based as least in part on a set of usage data generated
(Continued)

by one or more other articles of PPE of a same type as the article of PPE; and one or more computer processors configured to: detect the safety event signature in the stream of usage data based on processing the stream of usage data with the model, and generate an output in response to detecting the safety event signature.

56 Claims, 13 Drawing Sheets

Related U.S. Application Data

(60) Provisional application No. 62/408,634, filed on Oct. 14, 2016.

(51) Int. Cl.
  *A62B 9/00* (2006.01)
  *A62B 18/00* (2006.01)
  *A62B 27/00* (2006.01)
  *A61F 9/06* (2006.01)

(52) U.S. Cl.
  CPC ........ *A62B 27/00* (2013.01); *G06F 17/30516* (2013.01)

(56) References Cited

U.S. PATENT DOCUMENTS

| | | | |
|---|---|---|---|
| 5,245,994 A | 9/1993 | Chang | |
| 5,666,949 A | 9/1997 | Debe | |
| 5,796,341 A | 8/1998 | Stratiotis | |
| 6,186,140 B1* | 2/2001 | Hoague | B01D 29/60 128/201.25 |
| 6,456,199 B1 | 9/2002 | Michael | |
| 6,472,988 B1* | 10/2002 | Feld | A62B 9/006 340/539.1 |
| 6,734,393 B1 | 5/2004 | Friedl | |
| 6,887,293 B1* | 5/2005 | Abad | B05B 15/1248 427/378 |
| 7,019,652 B2* | 3/2006 | Richardson | A62B 7/00 128/202.22 |
| 7,080,414 B1 | 7/2006 | Montero | |
| 7,592,911 B1* | 9/2009 | Hudgens | G07C 9/00111 307/326 |
| 7,768,409 B2* | 8/2010 | Parias | F17C 13/003 340/539.1 |
| 8,294,580 B2* | 10/2012 | Witwer | G06Q 10/06 340/539.1 |
| 8,316,850 B2 | 11/2012 | Grilliot et al. | |
| 2003/0000001 A1 | 1/2003 | McDonald et al. | |
| 2004/0004547 A1* | 1/2004 | Appelt | G08B 21/02 340/573.1 |
| 2004/0100384 A1* | 5/2004 | Chen | G07C 9/00111 340/572.1 |
| 2005/0114154 A1* | 5/2005 | Wolkowicz | G06Q 30/02 340/539.12 |
| 2006/0044140 A1 | 3/2006 | Berg | |
| 2006/0085367 A1* | 4/2006 | Genovese | G06Q 10/00 706/44 |
| 2006/0125623 A1* | 6/2006 | Appelt | A61B 5/02055 340/521 |
| 2007/0078528 A1* | 4/2007 | Anke | G07C 5/006 700/21 |
| 2008/0018472 A1* | 1/2008 | Dasilva | G08B 25/016 340/572.4 |
| 2008/0021919 A1* | 1/2008 | Kaartinen | G06Q 10/087 |
| 2008/0241805 A1* | 10/2008 | Schantz | C23C 16/4402 434/218 |
| 2008/0302360 A1 | 12/2008 | Chambers | |
| 2009/0125460 A1* | 5/2009 | Hewison | G06N 3/004 706/11 |
| 2009/0210989 A1 | 8/2009 | Becker | |
| 2009/0231423 A1 | 9/2009 | Becker | |
| 2010/0107292 A1 | 5/2010 | Chevallier | |
| 2011/0056496 A1 | 3/2011 | Tilley | |
| 2011/0227700 A1* | 9/2011 | Hamerly | A62B 9/006 340/10.1 |
| 2013/0063550 A1 | 3/2013 | Ritchey | |
| 2013/0139816 A1 | 6/2013 | Proctor | |
| 2013/0144130 A1* | 6/2013 | Russell | A61B 5/0205 600/301 |
| 2013/0291271 A1 | 11/2013 | Becker | |
| 2015/0010158 A1 | 1/2015 | Broadley | |
| 2015/0181972 A1 | 7/2015 | Djerassi | |
| 2016/0073722 A1 | 3/2016 | Eustace | |
| 2016/0106174 A1 | 4/2016 | Chung | |
| 2016/0355262 A1 | 12/2016 | Sharma | |
| 2017/0022807 A1 | 1/2017 | Dursun | |
| 2017/0330444 A1 | 11/2017 | M R | |

FOREIGN PATENT DOCUMENTS

| | | |
|---|---|---|
| WO | WO 2009/141474 | 11/2009 |
| WO | WO 2016/089708 | 6/2016 |

OTHER PUBLICATIONS

Machine Learning from Wikipedia, the free encyclopedia, retrieved from the internet Mar. 16, 2016, pp. 1-13.
U.S. Appl. No. 15/190,564, Restriction Requirement, dated Sep. 19, 2016.
U.S. Appl. No. 15/190,564, Response to Restriction Requirement dated Sep. 19, 2016, Response dated Nov. 15, 2016.
U.S. Appl. No. 15/190,564, Examiner-Initiated Interview Summary, OA, dated Feb. 7, 2017.
U.S. Appl. No. 15/190,564, Response to Examiner-Initiated Interview Summary, OA dated Feb. 7, 2017, Response dated May 8, 2017.
U.S. Appl. No. 15/190,564, OA Final, dated Aug. 9, 2017.
U.S. Appl. No. 15/190,564, Response to OA Final dated Aug. 9, 2017, Response dated Nov. 9, 2017.
U.S. Appl. No. 15/190,564, Interview Summary, dated Nov. 14, 2017.
U.S. Appl. No. 15/631,950, OA dated Nov. 27, 2017.
PCT/US2017/038846, International Search Report dated Sep. 13, 2017.
PCT/US2017/038846, Written Opinion of the ISA dated Sep. 13, 2017.
PCT/US2017/038983, International Search Report dated Sep. 28, 2017.
PCT/US2017/038983, Written Opinion of the ISA dated Sep. 28, 2017.
PCT/US2017/038983, Demand and Response to Written Opinion of the ISA dated Sep. 28, 2017, Response dated Dec. 19, 2017.
PCT/US2017/039041, International Search Report dated Sep. 28, 2017.
PCT/US2017/039041, Written Opinion of the ISA dated Sep. 28, 2017.
PCT/US2017/039041, Demand and Response to Written Opinion of the ISA dated Sep. 28, 2017, Response dated Dec. 19, 2017.
U.S. Appl. No. 15/631,950—Amendment and Response Under 37 C.F.R. §1.111 dated Feb. 27, 2018.
U.S. Appl. No. 15/190,564—Office Action dated Jan. 9, 2018.
New York Times article ""Pogonip" in Pittsburg Air" published Jan. 12, 1910.
PCT/US2017/039003, International Search Report dated Sep. 14, 2017.
PCT/US2017/039003, Written Opinion of the ISA dated Sep. 14, 2017.
PCT/US2017/039015, International Search Report dated Sep. 21, 2017.
PCT/US2017/039015, Written Opinion of the ISA dated Sep. 21, 2017.
PCT/US2017/039030, International Search Report dated Aug. 10, 2017.

(56) References Cited

OTHER PUBLICATIONS

PCT/US2017/039030, Written Opinion of the ISA dated Aug. 10, 2017,
"Modeling Human Performance in Chemical Protective Suits", Murray, 2010, Proceedings of the 2010 Industrial Engineering Research Conference.
"Outbreak Agent: Intelligent Wearable Technology for Hazardous Environments", Rogers, 1997, IEEE, 0-7803-4053, pp. 3198-3203.
"Artificial Intelligence" Russell, 2003, Prentice Hall.
"Evaluating the Physiological Performance of a Liquid Cooling Garment Used to Control Heat Stress in Hazmat Protective Ensembles", Semeniuk, 2005, Journal of ASTM International, Feb. 2005, vol. 2, No. 2.
U.S. Appl. No. 15/190,564, Response to Office Action dated Jan. 9, 2018, Response filed Apr. 9, 2018.

* cited by examiner

PERSONAL PROTECTIVE EQUIPMENT (PPE) WITH ANALYTICAL STREAM PROCESSING FOR SAFETY EVENT DETECTION

This application is a continuation-in-part of U.S. application Ser. No. 15/190,564, filed Jun. 23, 2016 and further claims the benefit of U.S. Provisional Application 62/408,634 filed Oct. 14, 2016, the entire content of each of which are hereby expressly incorporated by reference herein.

TECHNICAL FIELD

The present disclosure relates to the field of personal protective equipment. More specifically, the present disclosure relates to personal protective equipment that generate data.

BACKGROUND

Personal protective equipment (PPE) may be used to protect a user (e.g., a worker) from harm or injury from a variety of causes. For example, fall protection equipment is important safety equipment for workers operating at potentially harmful or even deadly heights. To help ensure safety in the event of a fall, workers often wear safety harnesses connected to support structures with fall protection equipment such as lanyards, energy absorbers, self-retracting lifelines (SRLs), descenders, and the like. An SRL typically includes a lifeline that is wound about a biased drum rotatably connected to a housing. Movement of the lifeline causes the drum to rotate as the lifeline is extended out from and retracted into the housing. When working in areas where there is known to be, or there is a potential of there being, dusts, fumes, gases or other contaminants that are potentially hazardous or harmful to health, it is usual for a worker to use a respirator or a clean air supply source. While a large variety of respiratory devices are available, some commonly used devices include powered air purifying respirators (PAPR) and a self-contained breathing apparatus (SCBA). Other PPE may include, as non-limiting examples, hearing protection, head protection (e.g., visors, hard hats, or the like), protective clothing, or the like. In some examples, various personal protective equipment may generate various types of data.

SUMMARY

The techniques of this disclosure relate to processing streams of usage data from personal protective equipment (PPE), such as fall protection equipment, respirators, head protection, hearing protection, or the like. For example, a variety of PPE may be fitted with electronic sensors that generate streams of usage data regarding status or operation of the PPE. According to aspects of this disclosure, an analytical stream processing component may be configured to detect a safety event signature in the stream of usage data based on processing the stream of usage data with a model that is trained based on usage data from other PPE of the same type. The analytical stream processing component may be incorporated in the PPE, in a hub that communicates with the PPE via short-range wireless communication protocols, and/or one or more servers configured to receive the usage data streams. According to aspects of this disclosure, the particular component responsible for processing the usage data streams may be determined based on a variety of factors.

In some instances, techniques may be used for monitoring and predicting safety events that correspond to the safety event signatures. In general, a safety event may refer to activities of a user of PPE, a condition of the PPE, or a hazardous environmental condition to name only a few examples. In some examples, a safety event may be an injury or worker condition, workplace harm, or regulatory violation. In still other examples, the safety event may include at least one of an abnormal condition of worker behavior, an abnormal condition of the article of PPE, an abnormal condition in the work environment, or a violation of a safety regulation. For example, in the context of fall protection equipment, a safety event may be misuse of the fall protection equipment, a user of the fall equipment experiencing a fall, or a failure of the fall protection equipment. In the context of a respirator, a safety event may be misuse of the respirator, a user of the respirator not receiving an appropriate quality and/or quantity of air, or failure of the respirator. A safety event may also be associated with a hazard in the environment in which the PPE is located. In some examples, occurrence of a safety event associated with the article of PPE may include a safety event in the environment in which the PPE is used or a safety event associated with a worker using the article of PPE. In some examples, a safety event may be an indication that PPE, a worker, and/or a worker environment are operating, in use, or acting in a way that is normal operation, where normal operation is a predetermined or predefined condition of acceptable or safe operation, use, or activity.

By implementing a model that identifies safety event signatures for safety events in streams of usage data relating to the worker, PPE, and/or environment, the system may more quickly and accurately identify safety events that may affect the worker's safety, the operation of the articles of PPE, and/or the condition of the work environment to name only a few examples. Rather than evaluating the cause of a safety event long after the safety event has occurred (and potential harm to the worker has occurred), the model, which may define relations between usage data over defined time durations and the likelihood of safety event signatures that correspond to safety events, may proactively and preemptively generate notifications and/or alter the operation of PPE before or immediately when a safety event occurs. Moreover, the system of this disclosure may flexibly predict the likelihood of a safety event from a particular set of usage data that the model has not yet been trained with, thereby eliminating the need to implement explicit work rules that may otherwise be too expansive in size to practically implement and process for each new set of usage data.

In some examples, a system includes an article of personal protective equipment (PPE) having at least one sensor configured to generate a stream of usage data; and an analytical stream processing component comprising: a communication component that receives the stream of usage data from the at least one sensor of the article of PPE; a memory configured to store at least a portion of the stream of usage data and at least one model for detecting a safety event signature, wherein the at least one model is trained based as least in part on a set of usage data generated, prior to receiving the stream of usage data, by one or more other articles of PPE of a same type as the article of PPE; and one or more computer processors configured to: detect the safety event signature in the stream of usage data based on processing the stream of usage data with the model, and generate an output in response to detecting the safety event signature.

In some examples, a system includes a set of a sensors that generate one or more streams of usage data corresponding to at least one of an article of PPE, a worker, or a work environment; and an analytical stream processing component comprising: a communication component that receives the one or more streams of usage data from the set of sensors that generate the one or more streams of usage data corresponding to at least one of an article of PPE, a worker, or a work environment; a memory configured to store at least a portion of the one or more streams of usage data and at least one model for detecting a safety event signature, wherein the at least one model is trained based as least in part on a set of usage data generated, prior to receiving the one or more streams of usage data, by one or more other articles of PPE, workers, or work environments of a same type as the at least one of the article of PPE, the worker, or the work environment; and one or more computer processors configured to: detect the safety event signature in the one or more streams of usage data based on processing the one or more streams of usage data with the model, and generate an output in response to detecting the safety event signature.

In some examples, a computing device includes: a memory; and one or more computer processors that: receive a stream of usage data from the at least one sensor of an article of PPE, wherein the article of PPE has at least one sensor configured to generate the stream of usage data; store at least a portion of the stream of usage data and at least one model for detecting a safety event signature, wherein the at least one model is trained based as least in part on a set of usage data generated, prior to receiving the stream of usage data, by one or more other articles of PPE of a same type as the article of PPE; detect the safety event signature in the stream of usage data based on processing the stream of usage data with the model; and generate an output in response to detecting the safety event signature.

The details of one or more examples of the disclosure are set forth in the accompanying drawings and the description below. Other features, objects, and advantages of the disclosure will be apparent from the description and drawings, and from the claims.

BRIEF DESCRIPTION OF DRAWINGS

FIGS. 10-13 illustrate example user interfaces for representing usage data from one or more respirators, according to aspects of this disclosure

DETAILED DESCRIPTION

Figure 1:
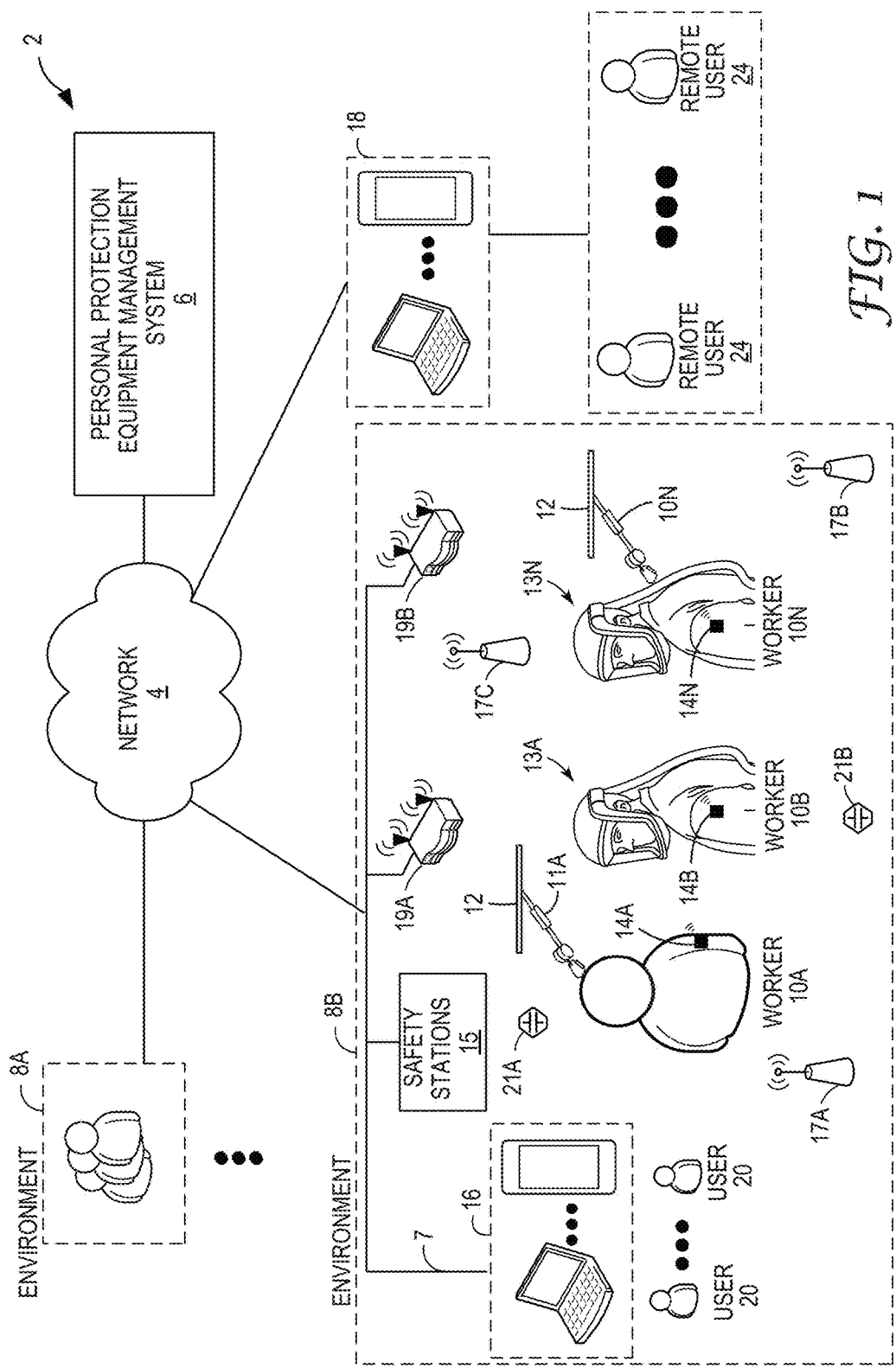
FIG. 1 is a block diagram illustrating an example system in which personal protection equipment (PPEs) having embedded sensors and communication capabilities are utilized within a number of work environments and are managed by a personal protection equipment management system in accordance with various techniques of this disclosure.

FIG. 1 is a block diagram illustrating an example computing system 2 that includes a personal protection equipment management system (PPEMS) 6 for managing personal protection equipment. As described herein, PPEMS allows authorized users to perform preventive occupational health and safety actions and manage inspections and maintenance of safety protective equipment. By interacting with PPEMS 6, safety professionals can, for example, manage area inspections, worker inspections, worker health and safety compliance training.

In general, PPEMS 6 provides data acquisition, monitoring, activity logging, reporting, predictive analytics and alert generation. For example, PPEMS 6 includes an underlying analytics and safety event prediction engine and alerting system in accordance with various examples described herein. As further described below, PPEMS 6 provides an integrated suite of personal safety protection equipment management tools and implements various techniques of this disclosure. That is, PPEMS 6 provides an integrated, end-to-end system for managing personal protection equipment, e.g., safety equipment, used by workers 10 within one or more physical environments 8, which may be construction sites, mining or manufacturing sites or any physical environment. The techniques of this disclosure may be realized within various parts of computing environment 2. Although certain examples of this disclosure are provided with respect to certain types of PPE for illustration purposes, the systems, techniques, and devices of this disclosure are applicable to any type of PPE.

As shown in the example of FIG. 1, system 2 represents a computing environment in which a computing device within of a plurality of physical environments 8A, 8B (collectively, environments 8) electronically communicate with PPEMS 6 via one or more computer networks 4. Each of physical environment 8 represents a physical environment, such as a work environment, in which one or more individuals, such as workers 10, utilize personal protection equipment while engaging in tasks or activities within the respective environment.

In this example, environment 8A is shown as generally as having workers 10, while environment 8B is shown in expanded form to provide a more detailed example. In the example of FIG. 1, a plurality of workers 10A-10N are shown as utilizing PPE, such as fall protection equipment (shown in this example as self-retracting lifelines (SRLs) 11A-11N) attached to safety support structure 12 and respirators 13A-13N. As described in greater detail herein, in other examples, workers 10 may utilize a variety of other PPE that is compatible with the techniques described herein, such as hearing protection, head protection, safety clothing, or the like.

As further described herein, each of SRLs 11 includes embedded sensors or monitoring devices and processing electronics configured to capture data in real-time as a user (e.g., worker) engages in activities while wearing the fall protection equipment. In some examples, smart hooks that determine whether a hook is secured or unsecured to a fixed anchoring point may also be within the spirit and scope of fall protection PPE in this disclosure. For example, as described in greater detail with respect to the example shown in FIG. 3, SRLs may include a variety of electronic sensors such as one or more of an extension sensor, a tension sensor, an accelerometer, a location sensor, an altimeter, one or more environment sensors, and/or other sensors for measuring operations of SRLs 11. In addition, each of SRLs 11 may include one or more output devices for outputting data that is indicative of operation of SRLs 11 and/or generating and outputting communications to the respective worker 10. For example, SRLs 11 may include one or more devices to generate audible feedback (e.g., one or more speakers), visual feedback (e.g., one or more displays, light emitting diodes (LEDs) or the like), or tactile feedback (e.g., a device that vibrates or provides other haptic feedback).

Respirators 13 may also include embedded sensors or monitoring devices and processing electronics configured to capture data in real-time as a user (e.g., worker) engages in activities while wearing the respirators. For example, as described in greater detail herein, respirators 13 may include a number of components (e.g., a head top, a blower, a filter, and the like) respirators 13 may include a number of sensors for sensing or controlling the operation of such components. A head top may include, as examples, a head top visor position sensor, a head top temperature sensor, a head top motion sensor, a head top impact detection sensor, a head top position sensor, a head top battery level sensor, a head top head detection sensor, an ambient noise sensor, or the like. A blower may include, as examples, a blower state sensor, a blower pressure sensor, a blower run time sensor, a blower temperature sensor, a blower battery sensor, a blower motion sensor, a blower impact detection sensor, a blower position sensor, or the like. A filter may include, as examples, a filter presence sensor, a filter type sensor, or the like. Each of the above-noted sensors may generate usage data. While FIG. 1 is described with respect to SRLs 11 and respirators 13, as described herein, the techniques of this disclosure may also be applied to a variety of other PPE.

In general, each of environments 8 include computing facilities (e.g., a local area network) by which SRLs 11 and respirators 13 are able to communicate with PPEMS 6. For example, environments 8 may be configured with wireless technology, such as 602.11 wireless networks, 602.15 ZigBee networks, and the like. In the example of FIG. 1, environment 8B includes a local network 7 that provides a packet-based transport medium for communicating with PPEMS 6 via network 4. In addition, environment 8B includes a plurality of wireless access points 19A, 19B that may be geographically distributed throughout the environment to provide support for wireless communications throughout the work environment.

Each of SRLs 11 and respirators 13 is configured to communicate data, such as sensed motions, events and conditions, via wireless communications, such as via 602.11 WiFi protocols, Bluetooth protocol or the like. SRLs 11 and respirators 13 may, for example, communicate directly with a wireless access point 19. As another example, each worker 10 may be equipped with a respective one of wearable communication hubs 14A-14N that enable and facilitate communication between SRLs 11, respirators 13 and PPEMS 6. For example, PPE for the respective worker 10 may communicate with a respective communication hub 14 via Bluetooth or other short range protocol, and the communication hubs may communicate with PPEMs 6 via wireless communications processed by wireless access points 19. Although shown as wearable devices, hubs 14 may be implemented as stand-alone devices deployed within environment 8B. In some examples, hubs 14 may be articles of PPE.

In general, each of hubs 14 operates as a wireless device for SRLs 11, respirators 13, and/or other PPE relaying communications to and from the PPE, and may be capable of buffering usage data in case communication is lost with PPEMS 6. Moreover, each of hubs 14 is programmable via PPEMS 6 so that local alert rules may be installed and executed without requiring a connection to the cloud. As such, each of hubs 14 provides a relay of streams of usage data from SRLs 11, respirators 13, and/or other PPEs within the respective environment, and provides a local computing environment for localized alerting based on streams of events in the event communication with PPEMS 6 is lost.

As shown in the example of FIG. 1, an environment, such as environment 8B, may also include one or more wireless-enabled beacons, such as beacons 17A-17C, that provide accurate location information within the work environment. For example, beacons 17A-17C may be GPS-enabled such that a controller within the respective beacon may be able to precisely determine the position of the respective beacon. Based on wireless communications with one or more of beacons 17, a given article of PPE or communication hub 14 worn by a worker 10 is configured to determine the location of the worker within work environment 8B. In this way, event or usage data reported to PPEMS 6 may be stamped with positional information to aid analysis, reporting and analytics performed by the PPEMS.

In addition, an environment, such as environment 8B, may also include one or more wireless-enabled sensing stations, such as sensing stations 21A, 21B. Each sensing station 21 includes one or more sensors and a controller configured to output data indicative of sensed environmental conditions. Moreover, sensing stations 21 may be positioned within respective geographic regions of environment 8B or otherwise interact with beacons 17 to determine respective positions and include such positional information when reporting environmental data to PPEMS 6. As such, PPEMS 6 may be configured to correlate the sensed environmental conditions with the particular regions and, therefore, may utilize the captured environmental data when processing event data (also referred to as "usage data") received from SRLs 11, respirators 13, or other PPE. For example, PPEMS 6 may utilize the environmental data to aid generating alerts or other instructions for PPE and for performing predictive analytics, such as determining any correlations between certain environmental conditions (e.g., heat, humidity, visibility) with abnormal worker behavior or increased safety events. As such, PPEMS 6 may utilize current environmental conditions to aid prediction and avoidance of imminent safety events. Example environmental conditions that may be sensed by sensing devices 21 include but are not limited to temperature, humidity, presence of gas, pressure, visibility, wind, precipitation and the like.

In example implementations, an environment, such as environment 8B, may also include one or more safety stations 15 distributed throughout the environment to provide viewing stations for accessing PPEMs 6. Safety stations 15 may allow one of workers 10 to check out SRLs 11, respirators 13 and/or other safety equipment, verify that safety equipment is appropriate for a particular one of environments 8, and/or exchange data. For example, safety stations 15 may transmit alert rules, software updates, or firmware updates to SRLs 11, respirators 13 or other equipment. Safety stations 15 may also receive data cached on SRLs 11, respirators 13, hubs 14, and/or other safety equipment. That is, while SRLs 11, and respirators 13 and/or data hubs 14 may typically transmit usage data to network 4, in some instances, SRLs 11, respirators 13, and/or data hubs 14 may not have connectivity to network 4. In such instances, SRLs 11, respirators 13, and/or data hubs 14 may store usage data locally and transmit the usage data to safety stations 15 upon being in proximity with safety stations 15. Safety stations 15 may then upload the data from the equipment and connect to network 4.

In addition, each of environments 8 include computing facilities that provide an operating environment for end-user computing devices 16 for interacting with PPEMS 6 via network 4. For example, each of environments 8 typically includes one or more safety managers responsible for overseeing safety compliance within the environment. In general, each user 20 interacts with computing devices 16 to access PPEMS 6. Each of environments 8 may include systems that are described in this disclosure. Similarly, remote users may use computing devices 18 to interact with PPEMS via network 4. For purposes of example, the end-user computing devices 16 may be laptops, desktop computers, mobile devices such as tablets or so-called smart phones and the like.

Users 20, 24 interact with PPEMS 6 to control and actively manage many aspects of safely equipment utilized by workers 10, such as accessing and viewing usage records, analytics and reporting. For example, users 20, 24 may review usage information acquired and stored by PPEMS 6, where the usage information may include data specifying starting and ending times over a time duration (e.g., a day, a week, or the like), data collected during particular events, such as detected falls, sensed data acquired from the user, environment data, and the like. In addition, users 20, 24 may interact with PPEMS 6 to perform asset tracking and to schedule maintenance events for individual pieces of safety equipment, e.g., SRLs 11 and respirators 13, to ensure compliance with any procedures or regulations. PPEMS 6 may allow users 20, 24 to create and complete digital checklists with respect to the maintenance procedures and to synchronize any results of the procedures from computing devices 16, 18 to PPEMS 6.

Further, as described herein, PPEMS 6 integrates an event processing platform configured to process thousand or even millions of concurrent streams of events from digitally enabled PPEs, such as SRLs 11 and respirators 13. An underlying analytics engine of PPEMS 6 applies the inbound streams to historical data and models to compute assertions, such as identified safety event signatures which may include anomalies or predicted occurrences of safety events based on conditions or behavior patterns of workers 10. Further, PPEMS 6 provides real-time alerting and reporting to notify workers 10 and/or users 20, 24 of any predicted events, anomalies, trends, and the like.

The analytics engine of PPEMS 6 may, in some examples, process streams of usage data with respect to models to identify relationships or correlations between sensed worker data, environmental conditions, geographic regions and other factors and analyze the impact on safety events. PPEMS 6 may determine, based on the data acquired across populations of workers 10, which particular activities, possibly within certain geographic region, lead to, or are predicted to lead to, unusually high occurrences of safety events.

In this way, PPEMS 6 tightly integrates comprehensive tools for managing personal protection equipment with an underlying analytics engine and communication system to provide data acquisition, monitoring, activity logging, reporting, behavior analytics and alert generation. Moreover, PPEMS 6 provides a communication system for operation and utilization by and between the various elements of system 2. Users 20, 24 may access PPEMS to view results on any analytics performed by PPEMS 6 on data acquired from workers 10. In some examples, PPEMS 6 may present a web-based interface via a web server (e.g., an HTTP server) or client-side applications may be deployed for devices of computing devices 16, 18 used by users 20, 24, such as desktop computers, laptop computers, mobile devices such as smartphones and tablets, or the like.

In some examples, PPEMS 6 may provide a database query engine for directly querying PPEMS 6 to view acquired safety information, compliance information and any results of the analytic engine, e.g., by the way of dashboards, alert notifications, reports and the like. That is, users 24, 26, or software executing on computing devices 16, 18, may submit queries to PPEMS 6 and receive data corresponding to the queries for presentation in the form of one or more reports or dashboards. Such dashboards may provide various insights regarding system 2, such as baseline ("normal") operation across worker populations, identifications of any anomalous workers engaging in abnormal activities that may potentially expose the worker to risks, identifications of any geographic regions within environments 2 for which unusually anomalous (e.g., high) safety events have been or are predicted to occur, identifications of any of environments 2 exhibiting anomalous occurrences of safety events relative to other environments, and the like.

As illustrated in detail below, PPEMS 6 may simplify workflows for individuals charged with monitoring and ensure safety compliance for an entity or environment. That is, the techniques of this disclosure may enable active safety management and allow an organization to take preventative or correction actions with respect to certain regions within environments 8, particular articles of PPE or individual workers 10, define and may further allow the entity to implement workflow procedures that are data-driven by an underlying analytical engine.

As one example, the underlying analytical engine of PPEMS 6 may be configured to compute and present customer-defined metrics for worker populations within a given environment 8 or across multiple environments for an organization as a whole. For example, PPEMS 6 may be configured to acquire data and provide aggregated performance metrics and predicted behavior analytics across a worker population (e.g., across workers 10 of either or both of environments 8A, 8B). Furthermore, users 20, 24 may set benchmarks for occurrence of any safety incidences, and PPEMS 6 may track actual performance metrics relative to the benchmarks for individuals or defined worker populations.

As another example, PPEMS 6 may further trigger an alert if certain combinations of conditions are present, e.g., to accelerate examination or service of a safety equipment, such as one of SRLs 11, respirators 13, or the like. In this manner, PPEMS 6 may identify individual pieces of PPE or workers 10 for which the metrics do not meet the benchmarks and prompt the users to intervene and/or perform procedures to improve the metrics relative to the benchmarks, thereby ensuring compliance and actively managing safety for workers 10.

According to aspects of this disclosure, while certain techniques of FIG. 1 are described with respect to PPEMS 6, in other examples, one or more functions may be implemented by hubs 14, SRLs 11, respirators 13, or other PPE. For example, according to aspects of this disclosure, PPEMS 6, hubs 14, SRLs 11, respirators 13, or other PPE may include a selection component that applies rules with respect to which component is responsible for processing the streams of usage data. As described in greater detail herein, the selection rules may be static or dynamically determined based on, as examples, power consumption associated with detecting a safety event signature, a latency associated with detecting the anomaly, a connectivity status of the article of PPE, the worker device, the computing device, or the at least one server, a data type of the PPE data, a data volume of the PPE data, and the content of the PPE data.

Figure 2:
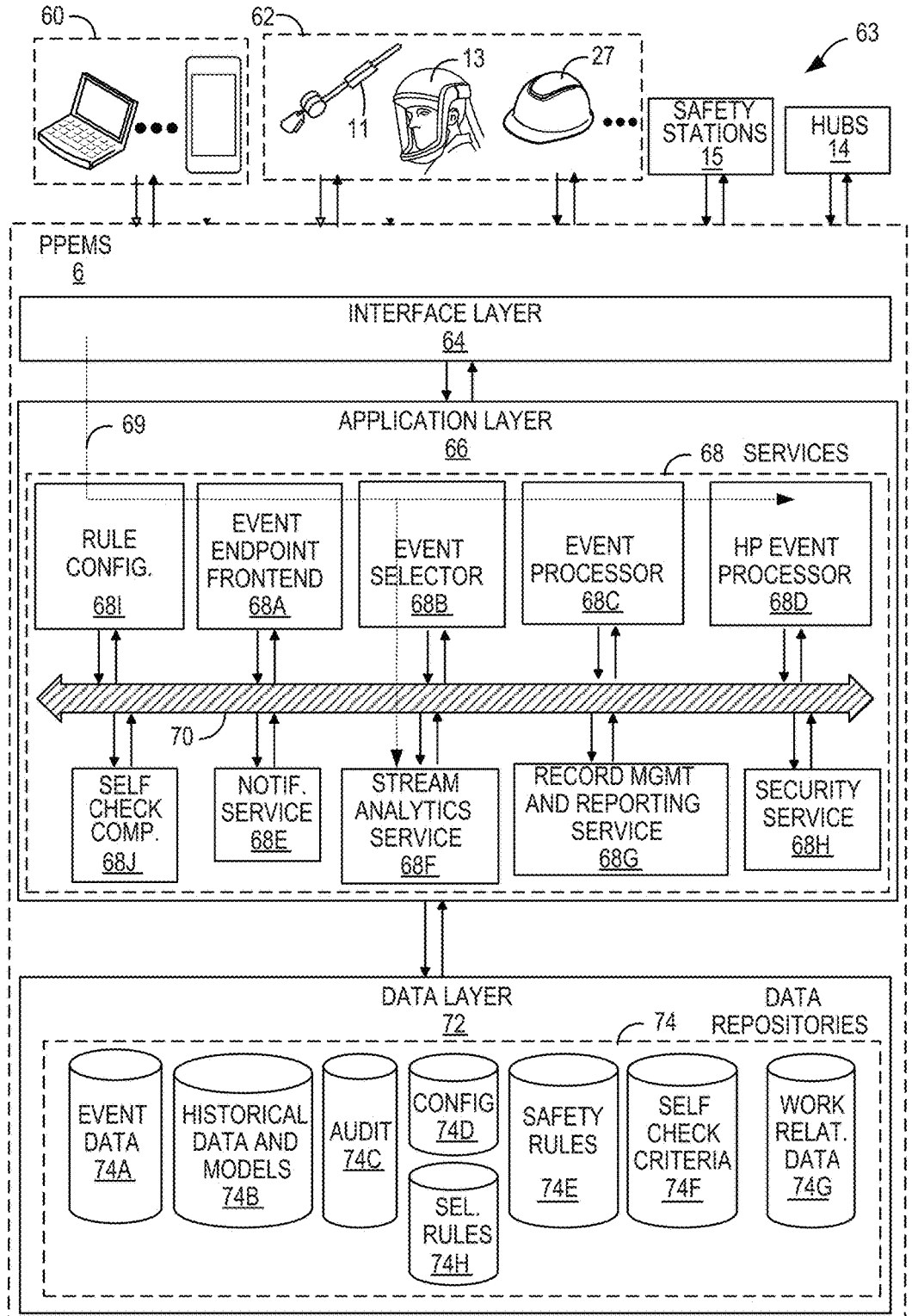
FIG. 2 is a block diagram illustrating an operating perspective of the personal protection equipment management system shown in FIG. 1.

FIG. 2 is a block diagram providing an operating perspective of PPEMS 6 when hosted as cloud-based platform capable of supporting multiple, distinct work environments 8 having an overall population of workers 10 that have a variety of communication enabled personal protection equipment (PPE), such as safety release lines (SRLs) 11, respirators 13, safety helmets 21, or other safety equipment. In the example of FIG. 2, the components of PPEMS 6 are arranged according to multiple logical layers that implement the techniques of the disclosure. Each layer may be implemented by a one or more modules comprised of hardware, software, or a combination of hardware and software.

In FIG. 2, personal protection equipment (PPE) 62, such as SRLs 11, respirators 13 and/or other equipment, either directly or by way of HUBs 14, as well as computing devices 60, operate as clients 63 that communicate with PPEMS 6 via interface layer 64. Computing devices 60 typically execute client software applications, such as desktop applications, mobile application, and web applications. Computing devices 60 may represent any of computing devices 16, 18 of FIG. 1. Examples of computing devices 60 may include, but are not limited to a portable or mobile computing device (e.g., smartphone, wearable computing device, tablet), laptop computers, desktop computers, smart television platforms, and servers, to name only a few examples.

As further described in this disclosure, PPE 62 communicate with PPEMS 6 (directly or via hubs 14) to provide streams of data acquired from embedded sensors and other monitoring circuitry and receive from PPEMS 6 alerts, configuration and other communications. Client applications executing on computing devices 60 may communicate with PPEMS 6 to send and receive information that is retrieved, stored, generated, and/or otherwise processed by services 68. For instance, the client applications may request and edit safety event information including analytical data stored at and/or managed by PPEMS 6. In some examples, client applications may request and display aggregate safety event information that summarizes or otherwise aggregates numerous individual instances of safety events and corresponding data acquired from PPE 62 and or generated by PPEMS 6. The client applications may interact with PPEMS 6 to query for analytics information about past and predicted safety events, behavior trends of workers 10, to name only a few examples. In some examples, the client applications may output for display information received from PPEMS 6 to visualize such information for users of clients 63. As further illustrated and described in below, PPEMS 6 may provide information to the client applications, which the client applications output for display in user interfaces.

Clients applications executing on computing devices 60 may be implemented for different platforms but include similar or the same functionality. For instance, a client application may be a desktop application compiled to run on a desktop operating system, such as Microsoft Windows, Apple OS X, or Linux, to name only a few examples. As another example, a client application may be a mobile application compiled to run on a mobile operating system, such as Google Android, Apple iOS, Microsoft Windows Mobile, or BlackBerry OS to name only a few examples. As another example, a client application may be a web application such as a web browser that displays web pages received from PPEMS 6. In the example of a web application, PPEMS 6 may receive requests from the web application (e.g., the web browser), process the requests, and send one or more responses back to the web application. In this way, the collection of web pages, the client-side processing web application, and the server-side processing performed by PPEMS 6 collectively provides the functionality to perform techniques of this disclosure. In this way, client applications use various services of PPEMS 6 in accordance with techniques of this disclosure, and the applications may operate within various different computing environment (e.g., embedded circuitry or processor of a PPE, a desktop operating system, mobile operating system, or web browser, to name only a few examples).

As shown in FIG. 2, PPEMS 6 includes an interface layer 64 that represents a set of application programming interfaces (API) or protocol interface presented and supported by PPEMS 6. Interface layer 64 initially receives messages from any of clients 63 for further processing at PPEMS 6. Interface layer 64 may therefore provide one or more interfaces that are available to client applications executing on clients 63. In some examples, the interfaces may be application programming interfaces (APIs) that are accessible over a network. Interface layer 64 may be implemented with one or more web servers. The one or more web servers may receive incoming requests, process and/or forward information from the requests to services 68, and provide one or more responses, based on information received from services 68, to the client application that initially sent the request. In some examples, the one or more web servers that implement interface layer 64 may include a runtime environment to deploy program logic that provides the one or more interfaces. As further described below, each service may provide a group of one or more interfaces that are accessible via interface layer 64.

In some examples, interface layer 64 may provide Representational State Transfer (RESTful) interfaces that use HTTP methods to interact with services and manipulate resources of PPEMS 6. In such examples, services 68 may generate JavaScript Object Notation (JSON) messages that interface layer 64 sends back to the client application 61 that submitted the initial request. In some examples, interface layer 64 provides web services using Simple Object Access Protocol (SOAP) to process requests from client applications. In still other examples, interface layer 64 may use Remote Procedure Calls (RPC) to process requests from clients 63. Upon receiving a request from a client application to use one or more services 68, interface layer 64 sends the information to application layer 66, which includes services 68.

As shown in FIG. 2, PPEMS 6 also includes an application layer 66 that represents a collection of services for implementing much of the underlying operations of PPEMS 6. Application layer 66 receives information included in requests received from client applications and further processes the information according to one or more of services 68 invoked by the requests. Application layer 66 may be implemented as one or more discrete software services executing on one or more application servers, e.g., physical or virtual machines. That is, the application servers provide runtime environments for execution of services 68. In some examples, the functionality interface layer 64 as described above and the functionality of application layer 66 may be implemented at the same server.

Application layer 66 may include one or more separate software services 68, e.g., processes that communicate, e.g., via a logical service bus 70 as one example. Service bus 70 generally represents a logical interconnections or set of interfaces that allows different services to send messages to other services, such as by a publish/subscription communication model. For instance, each of services 68 may subscribe to specific types of messages based on criteria set for the respective service. When a service publishes a message of a particular type on service bus 70, other services that subscribe to messages of that type will receive the message. In this way, each of services 68 may communicate information to one another. As another example, services 68 may communicate in point-to-point fashion using sockets or other communication mechanism. In still other examples, a pipeline system architecture could be used to enforce a workflow and logical processing of data a messages as they are process by the software system services. Before describing the functionality of each of services 68, the layers is briefly described herein.

Data layer 72 of PPEMS 6 represents a data repository that provides persistence for information in PPEMS 6 using one or more data repositories 74. A data repository, generally, may be any data structure or software that stores and/or manages data. Examples of data repositories include but are not limited to relational databases, multi-dimensional databases, maps, and hash tables, to name only a few examples. Data layer 72 may be implemented using Relational Database Management System (RDBMS) software to manage information in data repositories 74. The RDBMS software may manage one or more data repositories 74, which may be accessed using Structured Query Language (SQL). Information in the one or more databases may be stored, retrieved, and modified using the RDBMS software. In some examples, data layer 72 may be implemented using an Object Database Management System (ODBMS), Online Analytical Processing (OLAP) database or other suitable data management system.

As shown in FIG. 2, each of services 68A-68J ("services 68") is implemented in a modular form within PPEMS 6. Although shown as separate modules for each service, in some examples the functionality of two or more services may be combined into a single module or component. Each of services 68 may be implemented in software, hardware, or a combination of hardware and software. Moreover, services 68 may be implemented as standalone devices, separate virtual machines or containers, processes, threads or software instructions generally for execution on one or more physical processors.

In some examples, one or more of services 68 may each provide one or more interfaces that are exposed through interface layer 64. Accordingly, client applications of computing devices 60 may call one or more interfaces of one or more of services 68 to perform techniques of this disclosure.

In accordance with techniques of the disclosure, services 68 may include an event processing platform including an event endpoint frontend 68A, event selector 68B, event processor 68C and high priority (HP) event processor 68D. Event endpoint frontend 68A operates as a front end interface for receiving and sending communications to PPE 62 and hubs 14. In other words, event endpoint frontend 68A operates to as a front line interface to safety equipment deployed within environments 8 and utilized by workers 10. In some instances, event endpoint frontend 68A may be implemented as a plurality of tasks or jobs spawned to receive individual inbound communications of event streams 69 from the PPE 62 carrying data sensed and captured by sensors for a worker, PPE, and/or work environment. When receiving event streams 69, for example, event endpoint frontend 68A may spawn tasks to quickly enqueue an inbound communication, referred to as an event, and close the communication session, thereby providing high-speed processing and scalability. Each incoming communication may, for example, carry recently captured data representing sensed conditions, motions, temperatures, actions or other data, generally referred to as events. Communications exchanged between the event endpoint frontend 68A and the PPEs may be real-time or pseudo real-time depending on communication delays and continuity.

Event selector 68B operates on the stream of events 69 received from PPE 62 and/or hubs 14 via frontend 68A and determines, based on rules or classifications, priorities associated with the incoming events. Based on the priorities, event selector 68B enqueues the events for subsequent processing by event processor 68C or high priority (HP) event processor 68D. Additional computational resources and objects may be dedicated to HP event processor 68D so as to ensure responsiveness to critical events, such as incorrect usage of PPEs, use of incorrect filters and/or respirators based on geographic locations and conditions, failure to properly secure SRLs 11 and the like. Responsive to processing high priority events, HP event processor 68D may immediately invoke notification service 68E to generate alerts, instructions, warnings or other similar messages to be output to SRLs 11, hubs 14 and/or remote users 20, 24. Events not classified as high priority are consumed and processed by event processor 68C.

In general, event processor 68C or high priority (HP) event processor 68D operate on the incoming streams of events to update event data 74A within data repositories 74. In general, event data 74A may include all or a subset of usage data obtained from PPE 62. For example, in some instances, event data 74A may include entire streams of samples of data obtained from electronic sensors of PPE 62. In other instances, event data 74A may include a subset of such data, e.g., associated with a particular time period or activity of PPE 62. Event processors 68C, 68D may create, read, update, and delete event information stored in event data 74A. Event information for may be stored in a respective database record as a structure that includes name/value pairs of information, such as data tables specified in row/column format. For instance, a name (e.g., column) may be "worker ID" and a value may be an employee identification number. An event record may include information such as, but not limited to: worker identification, PPE identification, acquisition timestamp(s) and data indicative of one or more sensed parameters.

In addition, event selector 68B directs the incoming stream of events (e.g., usage data or event data) to stream analytics service 68F, which represents an example of an analytics engine configured to perform in depth processing of the incoming stream of events to perform real-time analytics. Stream analytics service 68F may, for example, be configured to process and compare multiple streams of event data 74A with historical data and models 74B in real-time as event data 74A is received. In this way, stream analytic service 68D may be configured to detect safety event signatures (e.g., anomalies, patterns, and the like), transform incoming event data values, trigger alerts upon detecting safety concerns based on conditions or worker behaviors. Historical data and models 74B may include, for example, specified safety rules, business rules and the like. In this way, historical data and models 74B may characterize activity of a user of SRL 11, e.g., as conforming to the safety rules, business rules, and the like. In addition, stream analytic service 68D may generate output for communicating to PPPE 62 by notification service 68F or computing devices 60 by way of record management and reporting service 68D.

Analytics service 68F may process inbound streams of events, potentially hundreds or thousands of streams of events, from enabled safety PPE 62 utilized by workers 10 within environments 8 to apply historical data and models 74B to compute assertions, such as identified safety event signatures, anomalies or predicted occurrences of imminent safety events based on conditions or behavior patterns of the workers. Analytics service 68D may publish the assertions to notification service 68F and/or record management by service bus 70 for output to any of clients 63. In some examples, at least one sensor that generates usage data that characterizes at least a worker associated with the article of PPE or a work environment; and to detect the safety event signature in the stream of usage, analytics service 68F processes the usage data that characterizes the worker associated with the article of PPE or the work environment.

In this way, analytics service 68F may be configured as an active safety management system that predicts imminent safety concerns and provides real-time alerting and reporting. In addition, analytics service 68F may be a decision support system that provides techniques for processing inbound streams of event data to generate assertions in the form of statistics, conclusions, and/or recommendations on an aggregate or individualized worker and/or PPE basis for enterprises, safety officers and other remote users. For instance, analytics service 68F may apply historical data and models 74B to determine, for a particular worker, the likelihood that a safety event is imminent for the worker based on detected behavior or activity patterns, environmental conditions and geographic locations. In some examples, analytics service 68F may determine whether a worker is currently impaired, e.g., due to exhaustion, sickness or alcohol/drug use, and may require intervention to prevent safety events. As yet another example, analytics service 68F may provide comparative ratings of workers or type of safety equipment in a particular environment 8.

Hence, analytics service 68F may maintain or otherwise use one or more models that provide risk metrics to predict safety events. Analytics service 68F may also generate order sets, recommendations, and quality measures. In some examples, analytics service 68F may generate user interfaces based on processing information stored by PPEMS 6 to provide actionable information to any of clients 63. For example, analytics service 68F may generate dashboards, alert notifications, reports and the like for output at any of clients 63. Such information may provide various insights regarding baseline ("normal") operation across worker populations, identifications of any anomalous workers engaging in abnormal activities that may potentially expose the worker to risks, identifications of any geographic regions within environments for which unusually anomalous (e.g., high) safety events have been or are predicted to occur, identifications of any of environments exhibiting anomalous occurrences of safety events relative to other environments, and the like.

Although other technologies can be used, in one example implementation, analytics service 68F utilizes machine learning when operating on streams of safety events so as to perform real-time analytics. That is, analytics service 68F includes executable code generated by application of machine learning to training data of event streams and known safety events to detect patterns. The executable code may take the form of software instructions or rule sets and is generally referred to as a model to which event streams 69 can be applied for detecting similar patterns and predicting upcoming events.

Analytics service 68F may, in some example, generate separate models for a particular worker, a particular population of workers, one or more articles of PPE or types of PPE, a particular environment, or combinations thereof. Analytics service 68F may update the models based on usage data received from PPE 62. For example, analytics service 68F may update the models for a particular worker, a particular population of workers, one or more articles of PPE or types of PPE a particular environment, or combinations thereof based on data received from PPE 62.

In some examples, analytics service 68F store at least a portion of a stream of usage data and at least one model for detecting a safety event signature. In some examples, the stream of usage data comprises metrics for a plurality of articles of PPE, workers, and/or work environments. As described in this disclosure, at least one model is trained based as least in part on a set of usage data generated, prior to receiving the stream of usage data, by one or more other articles of PPE of a same type as the article of PPE.

In some examples the "same type" may refer to identical but separate instances of PPE. In other examples the "same type" may not refer to identical instances of PPE. For instance, although not identical, a same type may refer to PPE in a same class or category of PPE, same model of PPE, or same set of one or more shared functional or physical characteristics, to name only a few examples. Similarly, a same type of work environment or worker may refer to identical but separate instances of work environment types or worker types. In other examples, although not identical, a same type may refer to a worker or work environment in a same class or category of worker or work environment or same set of one or more shared behavioral, physiological, environmental characteristics, to name only a few examples.

In some examples, safety event signature comprises at least one of an anomaly in a set of usage data, a pattern in a set of usage data, a particular set of occurrences of particular events over a defined period of time, a particular set of types of particular events over a defined period of time, a particular set of magnitudes of particular events over a defined period of time, or a value that satisfies a threshold (e.g., greater than, equal to, or less than). In some examples, the threshold is hard-coded, machine generated, and/or user-configurable. In some examples, a safety event signature may be a unique or a particularly defined profile of a set of events. In some examples, each respective event is generated at a same defined interval, wherein each respective event includes a respective set of values that correspond to a same set of defined metrics, and/or wherein respective sets of values in different respective events are different. Examples of a defined interval (which may be hard-coded, user-configurable, and/or machine-generated) include: 500 milliseconds, 1 minute, 5 minutes, 10 minutes, an interval in a range between 0-30 seconds, an interval in a range between 0-5 minutes, an interval in a range between 0-10 minutes, an interval in a range between 0-30 minutes, an interval in a range between 0-60 minutes, an interval in a range between 0-12 hours. In some examples, the set of defined metrics comprises one or more of a timestamp, characteristics of the article of PPE, characteristics of a worker associated with the article of PPE, or characteristics a work environment.

In some examples, analytics service 68F detects a safety event signature in a stream of usage data based on processing the stream of usage data with the model. To process the stream of usage data with the model, analytics service 68F may apply the usage data to the model. To apply the usage data to the model, analytics service 68F may generate a structure, such as a feature vector, in which the usage data is stored. The feature vector may include a set of values that correspond to metrics (e.g., characterizing PPE, worker, work environment, to name a few examples), where the set of values are included in the usage data. The model may receive the feature vector as input, and based on one or more relations defined by the model (e.g., probabilistic, deterministic or other functions within the knowledge of one of ordinary skill in the art) that has been trained, the model may output one or more probabilities or scores that indicate likelihoods of safety events based on the feature vector. Based on the safety event signature, analytics service 68F may generate an output in response. In some examples, at least one safety rule is mapped to at least one safety event, the at least one safety event is mapped to the safety event signature, and/or the safety event signature corresponds to at least the portion of a stream of usage data. As such, if at least a portion of a stream of usage data corresponds to a safety event signature, analytics service 68F may test and/or execute one or more safety rules that correspond to the safety event mapped to the safety event signature. In some examples, at least the portion of the stream of usage data is deleted after the one or more computer processors detect the safety event signature. For instance, the portion of the stream of usage data may be deleted after a threshold amount of time, or after being processed to detect the safety event signature.

In some examples, to generate output in response to detecting a safety event signature, analytics service 68F may cause one or more components of PPEMS 6 to send a notification to at least one of the article of PPE, a hub associated with a user and configured to communicate with the article of PPE and at least one remote computing device, or a computing device associated with person who is not the user. In some examples, to generate the output in response to detecting the safety event signature, analytics service 68F may cause one or more components of PPEMS 6 to send a notification that alters an operation of the article of PPE. In some examples, to generate output in response to detecting the safety event signature, analytics service 68F may cause one or more components of PPEMS 6 to output for display a user interface that indicates the safety event in association with at least one of a user, work environment, or the article of PPE. In some examples, to generate an output in response to detecting the safety event signature, the one or more processors may generate a user interface that is based at least in part on a safety event that corresponds to the safety event signature. In some examples, the user interface includes at least one input control that requires a responsive user input within a threshold time period, and in response to the threshold time period expiring without the responsive user input, PPEMS 6 may perform at least one operation based at least in part on the threshold time period expiring without the responsive user input. In some examples, an article of PPE comprises at least one of an air respirator system, a fall protection device, a hearing protector, a head protector, a garment, a face protector, an eye protector, a welding mask, or an exosuit.

In some examples, prior to detection of a safety event signature, analytics service 68F may determine, based at least in part on a data stream of usage data, that an article of PPE is operating in a normal state. A normal state may be a predefined state based on user input and/or machine-generated based on determined steady-state or acceptable conditions or use. In response to detection of a detection of the safety event signature, analytics service 68F may determine that the article of PPE is not operating in the normal state. For instance, prior to detecting the safety event signature, the article of PPE (or worker and/or worker environment) may have been operating in a steady-state or acceptable condition, which was subsequently followed by a safety event signature indicating an abnormal state or state other than the normal state. In some examples, a portion of a stream of usage data is a first portion of the stream of usage data, a safety event signature is a first safety event signature, a normal state corresponds to a second safety event signature, the first portion of the data stream corresponds to the first safety event signature, and a second portion of the data stream corresponds to the second safety event signature.

In some examples, a set of articles of PPE are associated with a user. Each article of PPE in the set of articles of PPE includes a motion sensor, such as an accelerometer, gyroscope or other device that can detect motion. Analytics service 68F may receive a respective stream of usage data from each respective motion sensor of each respective article of PPE of the set of articles of PPE. To detect a safety event signature, analytics service 68F may detect a safety event signature corresponding to a relative motion that is based at least in part on the respective stream of usage data from each respective motion sensor. That is, based on multiple different streams of usage data from different motion sensors positioned at different locations on the same user, analytics service 68F may determine a relative motion of the worker. In some examples, the safety event signature corresponds to a safety event that indicates ergonomic stress, and in some examples, analytics service 68F may determine that the ergonomic stress satisfies a threshold (e.g., greater than or equal to the threshold).

Alternatively, or in addition, analytics service 68F may communicate all or portions of the generated code and/or the machine learning models to hubs 14 (or PPE 62) for execution thereon so as to provide local alerting in near-real time to PPEs. Example machine learning techniques that may be employed to generate models 74B can include various learning styles, such as supervised learning, unsupervised learning, and semi-supervised learning. Example types of algorithms include Bayesian algorithms, Clustering algorithms, decision-tree algorithms, regularization algorithms, regression algorithms, instance-based algorithms, artificial neural network algorithms, deep learning algorithms, dimensionality reduction algorithms and the like. Various examples of specific algorithms include Bayesian Linear Regression, Boosted Decision Tree Regression, and Neural Network Regression, Back Propagation Neural Networks, the Apriori algorithm, K-Means Clustering, k-Nearest Neighbour (kNN), Learning Vector Quantization (LUQ), Self-Organizing Map (SOM), Locally Weighted Learning (LWL), Ridge Regression, Least Absolute Shrinkage and Selection Operator (LASSO), Elastic Net, and Least-Angle Regression (LARS), Principal Component Analysis (PCA) and Principal Component Regression (PCR).

Record management and reporting service 68G processes and responds to messages and queries received from computing devices 60 via interface layer 64. For example, record management and reporting service 68G may receive requests from client computing devices for event data related to individual workers, populations or sample sets of workers, geographic regions of environments 8 or environments 8 as a whole, individual or groups/types of PPE 62. In response, record management and reporting service 68G accesses event information based on the request. Upon retrieving the event data, record management and reporting service 68G constructs an output response to the client application that initially requested the information. In some examples, the data may be included in a document, such as an HTML document, or the data may be encoded in a JSON format or presented by a dashboard application executing on the requesting client computing device. For instance, as further described in this disclosure, example user interfaces that include the event information are depicted in the figures.

As additional examples, record management and reporting service 68G may receive requests to find, analyze, and correlate PPE event information. For instance, record management and reporting service 68G may receive a query request from a client application for event data 74A over a historical time frame, such as a user can view PPE event information over a period of time and/or a computing device can analyze the PPE event information over the period of time.

In example implementations, services 68 may also include security service 68H that authenticate and authorize users and requests with PPEMS 6. Specifically, security service 68H may receive authentication requests from client applications and/or other services 68 to access data in data layer 72 and/or perform processing in application layer 66. An authentication request may include credentials, such as a username and password. Security service 68H may query security data in data layer 72 to determine whether the username and password combination is valid. Configuration data 74D may include security data in the form of authorization credentials, policies, and any other information for controlling access to PPEMS 6. As described above, security data in data layer 72 may include authorization credentials, such as combinations of valid usernames and passwords for authorized users of PPEMS 6. Other credentials may include device identifiers or device profiles that are allowed to access PPEMS 6.

Security service 68H may provide audit and logging functionality for operations performed at PPEMS 6. For instance, security service 68H may log operations performed by services 68 and/or data accessed by services 68 in data layer 72. Security service 68H may store audit information such as logged operations, accessed data, and rule processing results in audit data 74C. In some examples, security service 68H may generate events in response to one or more rules being satisfied. Security service 68H may store data indicating the events in audit data 74C.

In the example of FIG. 2, a safety manager may initially configure one or more safety rules. As such, remote user 24 may provide one or more user inputs at computing device 18 that configure a set of safety rules for work environment 8A and 8B. For instance, a computing device 60 of the safety manager may send a message that defines or specifies the safety rules. Such message may include data to select or create conditions and actions of the safety rules. PPEMS 6 may receive the message at interface layer 64 which forwards the message to rule configuration component 68I. Rule configuration component 68I may be combination of hardware and/or software that provides for rule configuration including, but not limited to: providing a user interface to specify conditions and actions of rules, receive, organize, store, and update rules included in safety rules data store 74E.

Safety rules data store 74E may be a data store that includes data representing one or more safety rules. Safety rules data store 74E may be any suitable data store such as a relational database system, online analytical processing database, object-oriented database, or any other type of data store. When rule configuration component 68I receives data defining safety rules from computing device 60 of the safety manager, rule configuration component 68I may store the safety rules in safety rules data store 74E.

In the example of FIG. 2, PPEMS 6 also includes self-check component 68J, self-check criteria 74G and work relation data 74F. Self-check criteria 74G may include one or more self-check criterion as described in this disclosure. Work relation data 74F may include mappings between data that corresponds to PPE, workers, and work environments. Work relation data 74F may be any suitable datastore for storing, retrieving, updating and deleting data. RMRS 68G may store a mapping between the unique identifier of worker 10A and a unique device identifier of data hub 14A. Work relation data store 74F may also map a worker to an environment. In the example of FIG. 2, self-check component 68J may receive or otherwise determine data from work relation data 74F for data hub 14A, worker 10A, and/or PPE associated with or assigned to worker 10A. Based on this data, self-check component 68J may select one or more self-check criteria from self-check criteria 74G. Self-check component 68J may send the self-check criteria to data hub 14A.

According to aspects of this disclosure, the techniques for characterizing worker activity and detecting anomalies may be implemented by hubs 14, SRLs 11, respirators 13, or other PPE. For example, with respect to FIG. 2, PPEMS 6 includes selection rules 74H that include rules for determining the component for processing usage data. That is, rule configuration component 68I or another component of PPEMS 6 may determine whether to process usage data (or whether hubs 14 or PPE 62 is responsible for such processing) based on selection rules 74H.

Selection rules 74H may be static or dynamically determined based on, as examples, power consumption associated with detecting the anomaly. For example, in instances in which the processing componentry required for processing the usage data is relatively high and draws a relatively large amount of power, a selection rule may indicate that PPEMS 6 is responsible for the processing of the usage data, because PPE 62 and hubs 14 are typically battery powered.

In instances in which latency is a factor, a selection rule may indicate that processing of usage data to detect an anomaly is to be performed locally by hubs 14 or PPE 62.

For example, transmitting data to PPEMS 6 may take time (e.g., associated with transmitting the data via network 4). Some safety events may occur immediately or within a short time of an anomaly being present. In such instances, a selection rule may indicate that processing of usage data to detect an anomaly is to be performed locally by hubs 14 or PPE 62.

In another example, a selection rule may be based on a connectivity status of the article of PPE, a worker device (such as hub 14), a computing device (such as one of safety stations 15), or PPEMS 6. For example, in instances in which hubs 14 do not have connectivity to PPEMS 6 via network 4, hubs 14 may be responsible for processing the usage data and detecting anomalies. In instances in PPE 62 do not have connectivity to hubs 14 (or PPEMS 6), PPE 62 may be responsible for processing the usage data and detecting anomalies. In some examples, if PPE 62 and/or hubs 14 do not have connectivity to PPEMS 6, PPE 62 and/or hubs 14 may cache or batch usage data to send to PPEMS 6 or other computing devices. In some examples, PPE 62 and/or hubs 14 when sending cached or batched usage data, may only send a threshold number of most recent events as the usage data and/or may only send a threshold number of most relevant events as usage data.

In another example, a selection rule may be based on a data type of the PPE data. For example, certain PPE 62 may generate a plurality of data streams associated with a plurality of components or sensors. In this example, a selection rule may specify that a certain data type (e.g., from a particular component) is to be processed by a particular entity (e.g., one or PPE 62, hubs 14, and PPEMS 6), while another data type (e.g., from a different component) is to be processed by a different entity (e.g., one or PPE 62, hubs 14, and PPEMS 6).

In another example, a selection rule may be based on a data volume of the PPE data. For example, the selection rule may specify that large amounts of data are to be processed by PPEMS 6, e.g., due to potentially greater processing capacity. In other examples, the selection rule may specify that large amounts of data are to be processed by PPE 62 or hubs 14, e.g., due to energy consumption associated with transmitting such data.

In another example, a selection rule may be based on the content of the PPE data. For example, PPE 62 or hubs 14 may be configured to process data locally until identifying a context that is unexpected, such as a different environment, a different set of PPE, or the like. Based on the context of the usage data, PPE 62 or hubs 14 may send the usage data to PPEMS 6 for remote processing.

In general, selection rules 74H may be hierarchical in nature. That is, PPEMS 6 may typically be responsible for performing certain processing. In some instances, selection rules 74H may specify that at least a portion of the processing to detect anomalies is performed by hubs 14 (such as in a number of the above-described examples). In addition, selection rules 74H may specify that at least a portion of the processing to detect anomalies is performed by respective PPE 62.

Figure 3:
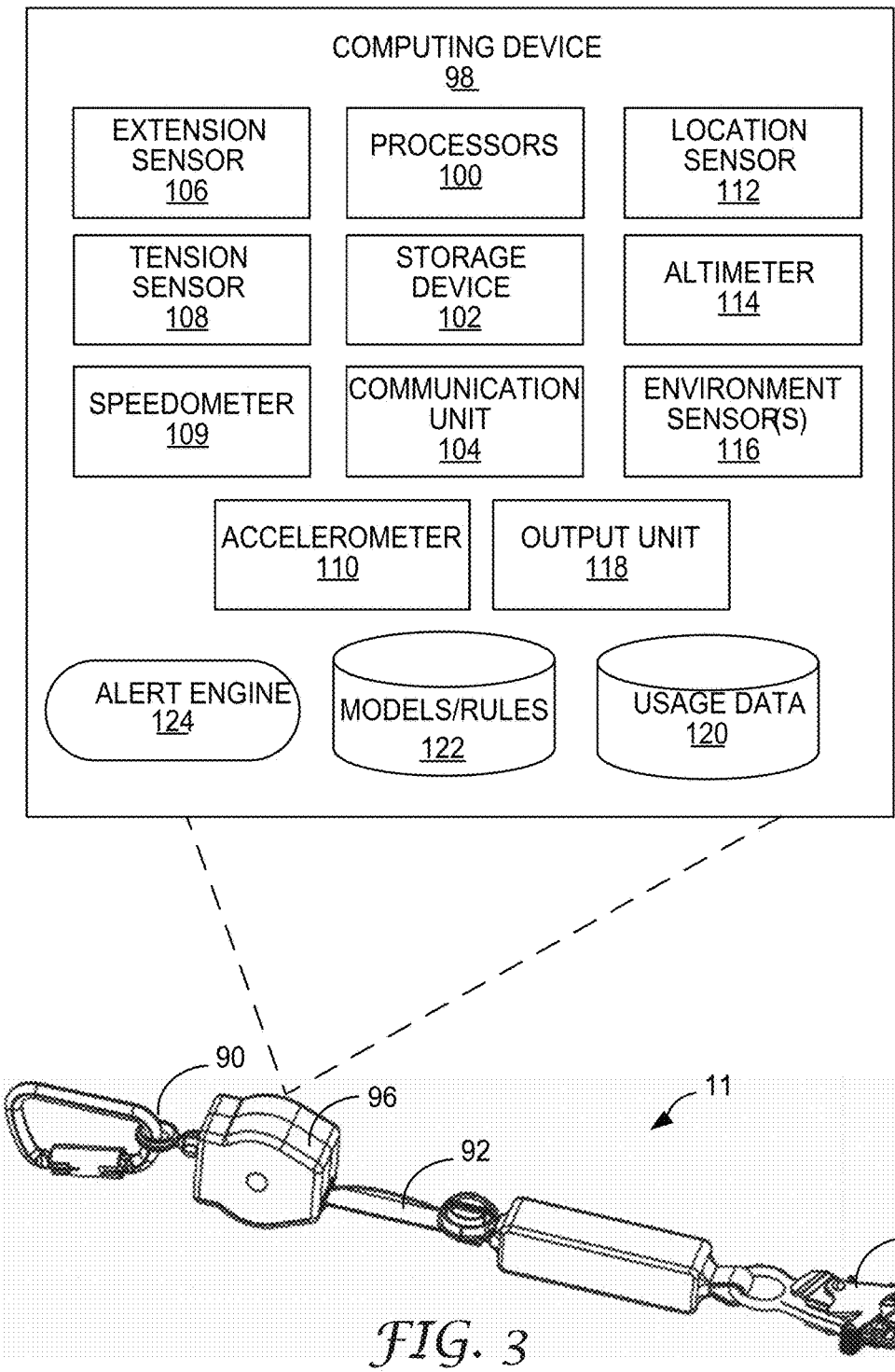
FIG. 3 is a conceptual diagram illustrating one example of a self-retracting lifeline (SRL), in accordance with aspects of this disclosure.

FIG. 3 illustrates an example of one of SRLs 11 in greater detail. In this example, SRL 11 includes a first connector 90 for attachment to an anchor, a lifeline 92, and a second connector 94 for attachment to a user (not shown). SRL 11 also includes housing 96 that houses an energy absorption and/or braking system and computing device 98. In the illustrated example, computing device 98 includes processors 100, storage device 102, communication unit 104, an extension sensor 106, a tension sensor 108, a speedometer 109, an accelerometer 110, a location sensor 112, an altimeter 114, one or more environment sensors 116, and output unit 118.

It should be understood that the architecture and arrangement of computing device 98 (and, more broadly, SRL 11) illustrated in FIG. 3 is shown for exemplary purposes only. In other examples, SRL 11 and computing device 98 may be configured in a variety of other ways having additional, fewer, or alternative components than those shown in FIG. 3. For example, in some instances, computing device 98 may be configured to include only a subset of components, such as communication unit 104 and extension sensor 106. Moreover, while the example of FIG. 3 illustrates computing device 98 as being integrated with housing 96, the techniques are not limited to such an arrangement.

First connector 90 may be anchored to a fixed structure, such as scaffolding or other support structures. Lifeline 92 may be wound about a biased drum that is rotatably connected to housing 96. Second connector 94 may be connected to a user (e.g., such as one of workers 10 (FIG. 1)). Hence, in some examples, first connector 90 may be configured as an anchor point that is connected to a support structure, and second connector 94 is configured to include a hook that is connected to a worker. In other examples, second connector 94 may be connected to an anchor point, while first connector 90 may be connected to a worker. As the user performs activities movement of lifeline 92 causes the drum to rotate as lifeline 92 is extended out and retracted into housing 96.

In general, computing device 98 may include a plurality of sensors that may capture real-time data regarding operation of SRL 11 and/or an environment in which SRL 11 is used. Such data may be referred to herein as usage data. The sensors may be positioned within housing 96 and/or may be located at other positions within SRL 11, such as proximate first connector 90 or second connector 94. Processors 100, in one example, are configured to implement functionality and/or process instructions for execution within computing device 98. For example, processors 100 may be capable of processing instructions stored by storage device 102. Processors 100 may include, for example, microprocessors, digital signal processors (DSPs), application specific integrated circuits (ASICs), field-programmable gate array (FPGAs), or equivalent discrete or integrated logic circuitry.

Storage device 102 may include a computer-readable storage medium or computer-readable storage device. In some examples, storage device 102 may include one or more of a short-term memory or a long-term memory. Storage device 102 may include, for example, random access memories (RAM), dynamic random access memories (DRAM), static random access memories (SRAM), magnetic hard discs, optical discs, flash memories, or forms of electrically programmable memories (EPROM) or electrically erasable and programmable memories (EEPROM).

In some examples, storage device 102 may store an operating system (not shown) or other application that controls the operation of components of computing device 98. For example, the operating system may facilitate the communication of data from electronic sensors (e.g., extension sensor 106, tension sensor 108, accelerometer 110, location sensor 112, altimeter 114, and/or environmental sensors 116) to communication unit 104. In some examples, storage device 102 is used to store program instructions for execution by processors 100. Storage device 102 may also be configured to store information within computing device 98 during operation.

Computing device 98 may use communication unit 104 to communicate with external devices via one or more wired or wireless connections. Communication unit 104 may include various mixers, filters, amplifiers and other components designed for signal modulation, as well as one or more antennas and/or other components designed for transmitting and receiving data. Communication unit 104 may send and receive data to other computing devices using any one or more suitable data communication techniques. Examples of such communication techniques may include TCP/IP, Ethernet, Wi-Fi, Bluetooth, 4G, LTE, to name only a few examples. In some instances, communication unit 104 may operate in accordance with the Bluetooth Low Energy (BLU) protocol.

Extension sensor 106 may be configured to generate and output data indicative of at least one an extension of lifeline 92 and a retraction of lifeline 92. In some examples, extension sensor 106 may generate data indicative of a length of extension of lifeline 92 or a length of retraction of lifeline 92. In other examples, extension sensor 106 may generate data indicative of an extension or retraction cycle. Extension sensor 106 may include one or more of a rotary encoder, an optical sensor, a Hall effect sensor, or another sensor for determining position and/or rotation. Extension sensor 106 may also include, in some examples, one or more switches that generate an output that indicates a full extension or full retraction of lifeline 92.

Tension sensor 108 may be configured to generate data indicative of a tension of lifeline 92, e.g., relative to second connector 90. Tension sensor 108 may include a force transducer that is placed in-line with lifeline 92 to directly or indirectly measure tension applied to SRL 11. In some instances, tension sensor 108 may include a strain gauge to measure static force or static tension on SRL 11. Tension sensor 108 may additionally or alternatively include a mechanical switch having a spring-biased mechanism is used to make or break electrical contacts based on a predetermined tension applied to SRL 11. In still other examples, tension sensor 108 may include one or more components for determining a rotation of friction brake of SRL 11. For example, the one or more components may include a sensor (e.g. an optical sensor, a Hall effect sensor, or the like) this is configured to determine relative motion between two components of a brake during activation of the braking system.

Speedometer 109 may be configured to generate data indicative of a speed of lifeline 92. For example, speedometer 109 may measure extension and/or retraction of lifeline (or receive such measurement from extension sensor 106) and apply the extension and/or retraction to a time scale (e.g., divide by time). Accelerometer 110 may be configured to generate data indicative of an acceleration of SRL 11 with respect to gravity. Accelerometer 110 may be configured as a single- or multi-axis accelerometer to determine a magnitude and direction of acceleration, e.g., as a vector quantity, and may be used to determine orientation, coordinate acceleration, vibration, shock, and/or falling.

Location sensor 112 may be configured to generate data indicative of a location of SRL 11 in one of environments 8. Location sensor 112 may include a Global Positioning System (GPS) receiver, componentry to perform triangulation (e.g., using beacons and/or other fixed communication points), or other sensors to determine the relative location of SRL 11.

Altimeter 114 may be configured to generate data indicative of an altitude of SRL 11 above a fixed level. In some examples, altimeter 114 may be configured to determine altitude of SRL 11 based on a measurement of atmospheric pressure (e.g., the greater the altitude, the lower the pressure).

Environment sensors 116 may be configured to generate data indicative of a characteristic of an environment, such as environments 8. In some examples, environment sensors 116 may include one or more sensors configured to measure temperature, humidity, particulate content, noise levels, air quality, or any variety of other characteristics of environments in which SRL 11 may be used.

Output unit 118 may be configured to output data that is indicative of operation of SRL 11, e.g., as measured by one or more sensors of SRL 11 (e.g., such as extension sensor 106, tension sensor 108, accelerometer 110, location sensor 112, altimeter 114, and/or environmental sensors 116). Output unit 118 may include instructions executable by processors 100 of computing device 98 to generate the data associated with operation of SRL 11. In some examples, output unit 118 may directly output the data from the one or more sensors of SRL 11. For example, output unit 118 may generate one or more messages containing real-time or near real-time data from one or more sensors of SRL 11 for transmission to another device via communication unit 104.

In other examples, output unit 118 (and/or processors 100) may process data from the one or more sensors and generate messages that characterize the data from the one or more sensors. For example, output unit 118 may determine a length of time that SRL 11 is in use, a number of extend and retract cycles of lifeline 92 (e.g., based on data from extension sensor 106), an average rate of speed of a user during use (e.g., based on data from extension sensor 106 or location sensor 112), an instantaneous velocity or acceleration of a user of SRL 11 (e.g., based on data from accelerometer 110), a number of lock-ups of a brake of lifeline 92 and/or a severity of an impact (e.g., based on data from tension sensor 108).

In some examples, output unit 118 may be configured to transmit the usage data in real-time or near-real time to another device (e.g., PPE 62) via communication unit 104. However, in some instances, communication unit 104 may not be able to communicate with such devices, e.g., due to an environment in which SRL 11 is located and/or network outages. In such instances, output unit 118 may cache usage data to storage device 102. That is, output unit 118 (or the sensors themselves) may store usage data to storage device 102, which may allow the usage data to be uploaded to another device upon a network connection becoming available.

Output unit 118 may also be configured to generate an audible, visual, tactile, or other output that is perceptible by a user of SRL 11. For example, output unit 118 may include one more user interface devices including, as examples, a variety of lights, displays, haptic feedback generators, speakers or the like. In one example, output unit 118 may include one or more light emitting diodes (LEDs) that are located on SRL 11 and/or included in a remote device that is in a field of view of a user of SRL 11 (e.g., indicator glasses, visor, or the like). In another example, output unit 118 may include one or more speakers that are located on SRL 11 and/or included in a remote device (e.g., earpiece, headset, or the like). In still another example, output unit 118 may include a haptic feedback generator that generates a vibration or other tactile feedback and that is included on SRL 11 or a remote device (e.g., a bracelet, a helmet, an earpiece, or the like).

Output unit 118 may be configured to generate the output based on operation of SRL 11. For example, output unit 118 may be configured to generate an output that indicates a status of SRL 11 (e.g. that SRL 11 is operating correctly or needs to be inspected, repaired, or replaced). As another example, output unit 118 may be configured to generate an output that indicates that SRL 11 is appropriate for the environment in which SRL 11 is located. In some examples, output unit 118 may be configured to generate an output data that indicates that the environment in which SRL 11 is located is unsafe (e.g., a temperature, particulate level, location or the like is potentially dangerous to a worker using SRL 11).

SRL 11 may, in some examples, be configured to store rules (e.g., such as safety rules 74E shown in FIG. 2), which may characterize a likelihood of a safety event, and output unit 118 may be configured to generate an output based on a comparison of operation of the SRL 11 (as measured by the sensors) to the rules. For example, SRL 11 may be configured to store rules to storage device 102 based on the above-described models and/or historical data from PPEMS 6. Storing and enforcing the rules locally may allow SRL 11 to determine the likelihood of a safety event with potentially less latency than if such a determination was made by PPEMS 6 and/or in instances in which there is no network connectivity available (such that communication with PPEMS 6 is not possible). In this example, output unit 118 may be configured to generate an audible, visual, tactile, or other output that alerts a worker using SRL 11 of potentially unsafe activities, anomalous behavior, or the like.

According to aspects of this disclosure, SRL 11 may receive, via communication unit 104, alert data, and output unit 118 may generate an output based on the alert data. For example, SRL 11 may receive alert data from one of hubs 14, PPEMS 6 (directly or via one or hubs 14), end-user computing devices 16, remote users using computing devices 18, safety stations 15, or other computing devices. In some examples, the alert data may be based on operation of SRL 11. For example, output unit 118 may receive alert data that indicates a status of the SRL, that SRL is appropriate for the environment in which SRL 11 is located, that the environment in which SRL 11 is located is unsafe, or the like.

In some examples, additionally or alternatively, SRL 11 may receive alert data associated with a likelihood of a safety event. For example, as noted above, PPEMS 6 may, in some examples, apply usage data from SRL 11 to historical data and models in order to compute assertions, such as detecting safety event signatures, anomalies or predicted occurrences of imminent safety events based on environmental conditions or behavior patterns of a worker using SRL 11. That is, PPEMS 6 may process streams of usage data to identify relationships or correlations between sensed data from SRL 11, environmental conditions of environment in which SRL 11 is located, a geographic region in which SRL 11 is located, and/or other factors. PPEMS 6 may determine, based on the data acquired across populations of workers 10, which particular activities, possibly within certain environment or geographic region, lead to, or are predicted to lead to, unusually high occurrences of safety events. SRL 11 may receive alert data from PPEMS 6 that indicates a relatively high likelihood of a safety event.

Output unit 118 may interpret the received alert data and generate an output (e.g., an audible, visual, or tactile output) to notify a worker using SRL 11 of the alert condition (e.g., that the likelihood of a safety event is relatively high, that the environment is dangerous, that SRL 11 is malfunctioning, that one or more components of SRL 11 need to be repaired or replaced, or the like). In some instances, output unit 118 (or processors 100) may additionally or alternatively interpret alert data to modify operation or enforce rules of SRL 11 in order to bring operation of SRL 11 into compliance with desired/less risky behavior. For example, output unit 118 (or processors 100) may actuate a brake on lifeline 92 in order to prevent lifeline 92 from extending from housing 96.

Hence, according to aspects of this disclosure, usage data from sensors of SRL 11 (e.g., data from extension sensor 106, tension sensor 108, accelerometer 110, location sensor 112, altimeter 114, environmental sensors 116, or other sensors) may be used in a variety of ways. According to some aspects, usage data may be used to determine usage statistics. For example, PPEMS 6 may determine, based on usage data from the sensors, an amount of time that SRL 11 is in use, a number of extension or retraction cycles of lifeline 92, an average rate of speed with which lifeline 92 is extended or retracted during use, an instantaneous velocity or acceleration with which lifeline 92 is extended or retracted during use, a number of lock-ups of lifeline 92, a severity of impacts to lifeline 92, or the like. In other examples, the above-noted usage statistics may be determined and stored locally (e.g., by SRL 11 or one of hubs 14).

According to aspects of this disclosure, PPEMS 6 may use the usage data to characterize activity of worker 10. For example, PPEMS 6 may establish patterns of productive and nonproductive time (e.g., based on operation of SRL 11 and/or movement of worker 10), categorize worker movements, identify key motions, and/or infer occurrence of key events. That is, PPEMS 6 may obtain the usage data, analyze the usage data using services 68 (e.g., by comparing the usage data to data from known activities/events), and generate an output based on the analysis.

In some examples, the usage statistics may be used to determine when SRL 11 is in need of maintenance or replacement. For example, PPEMS 6 may compare the usage data to data indicative of normally operating SRLs 11 in order to identify defects or anomalies. In other examples, PPEMS 6 may also compare the usage data to data indicative of a known service life statistics of SRLs 11. The usage statistics may also be used to provide an understanding how SRLs 11 are used by workers 10 to product developers in order to improve product designs and performance. In still other examples, the usage statistics may be used to gathering human performance metadata to develop product specifications. In still other examples, the usage statistics may be used as a competitive benchmarking tool. For example, usage data may be compared between customers of SRLs 11 to evaluate metrics (e.g. productivity, compliance, or the like) between entire populations of workers outfitted with SRLs 11.

Additionally or alternatively, according to aspects of this disclosure, usage data from sensors of SRLs 11 may be used to determine status indications. For example, PPEMS 6 may determine that worker 10 is connected to or disconnected from SRL 11. PPEMS 6 may also determine an elevation and/or position of worker 10 relative to some datum. PPEMS 6 may also determine that worker 10 is nearing a predetermined length of extraction of lifeline 92. PPEMS 6 may also determine a proximity of worker 10 to a hazardous area in one of environments 8 (FIG. 1). In some instances, PPEMS 6 may determine maintenance intervals for SRLs 11 based on use of SRLs 11 (as indicated by usage data) and/or environmental conditions of environments in which SRLs 11 are located. PPEMS 6 may also determine, based on usage data, whether SRL 11 is connected to an anchor/fixed structure and/or whether the anchor/fixed structure is appropriate.

Additionally or alternatively, according to aspects of this disclosure, usage data from sensors of SRLs 11 may be used to assess performance of worker 10 wearing SRL 11. For example, PPEMS 6 may, based on usage data from SRLs 11, recognize motion that may indicate a pending fall by worker 10. PPEMS 6 may also, based on usage data from SRLs 11, to recognize motion that may indicate fatigue. In some instances, PPEMS 6 may, based on usage data from SRLs 11, infer that a fall has occurred or that worker 10 is incapacitated. PPEMS 6 may also perform fall data analysis after a fall has occurred and/or determine temperature, humidity and other environmental conditions as they relate to the likelihood of safety events.

Additionally or alternatively, according to aspects of this disclosure, usage data from sensors of SRLs 11 may be used to determine alerts and/or actively control operation of SRLs 11. For example, PPEMS 6 may determine that a safety event such as a fall is imminent and active a brake of SRL 11. In some instances, PPEMS 6 may adjust the performance of the arrest characteristics to the fall dynamics. That is, PPEMS 6 may alert that control that is applied to SRL 11 based on the particular characteristics of the safety event (e.g., as indicated by usage data). PPEMS 6 may provide, in some examples, a warning when worker 10 is near a hazard in one of environments 8 (e.g., based on location data gathered from location sensor 112). PPEMS 6 may also lock out SRL 11 such that SRL 11 will not operate after SRL 11 has experienced an impact or is in need of service.

Again, PPEMS 6 may determine the above-described performance characteristics and/or generate the alert data based on application of the usage data to one or more safety models that characterizes activity of a user of SRL 11. The safety models may be trained based on historical data or known safety events. However, while the determinations are described with respect to PPEMS 6, as described in greater detail herein, one or more other computing devices, such as hubs 14 or SRLs 11 may be configured to perform all or a subset of such functionality.

In some examples, a safety model is trained using supervised and/or reinforcement learning techniques. The safety learning model may be implemented using any number of models for supervised and/or reinforcement learning, such as but not limited to, an artificial neural networks, a decision tree, naïve Bayes network, support vector machine, or k-nearest neighbor model, to name only a few examples. In some examples, PPEMS 6 initially trains the safety learning model based on a training set of metrics and corresponding to safety events. The training set may include a set of feature vectors, where each feature in the feature vector represents a value for a particular metric. As further example description, PPEMS 6 may select a training set comprising a set of training instances, each training instance comprising an association between usage data over a defined time duration and a safety event. The usage data may comprise one or more metrics that characterize at least one of a user, a work environment, or one or more articles of PPE. For each training instance in the training set, PPEMS 6 may modify, based on particular usage data over the defined time duration and a particular safety event of the training instance, the model to change a likelihood predicted by the model for the particular safety event signature associated with the safety event in response to subsequent usage data over the defined time duration applied to the model. In some examples, the training instances may be based on real-time or periodic data generated while PPEMS 6 managing data for one or more articles of PPE, workers, and/or work environments. As such, one or more training instances of the set of training instances may be generated from use of one or more articles of PPE after PPEMS 6 performs operations relating to the detection or prediction of a safety event for PPE, workers, and/or work environments that are currently in use, active, or in operation. In some examples, modification of the model may only occur for a defined period of time, after which the model returns to its state prior to the modification based on one or more training instances.

Some example metrics may include any characteristics or data described in this disclosure that relate to PPE, a worker, or a work environment, to name only a few examples. For instance, example metrics may include but are not limited to: worker identity, worker motion, worker location, worker age, worker experience, worker physiological parameters (e.g., heart rate, temperature, blood oxygen level, chemical compositions in blood, or any other measureable physiological parameter), worker reaction time to an event (e.g., an event requiring a worker response, an event not requiring a worker response or any other reaction time to an event) or any other data descriptive of a worker or worker behavior. Example metrics may include but are not limited to: PPE type, PPE usage, PPE age, PPE operations, or any other data descriptive of PPE or PPE use. Example metrics may include but are not limited to: work environment type, work environment location, work environment temperature, work environment hazards, work environment size, or any other data descriptive of a work environment.

Each feature vector may also have at least one corresponding safety event. As described in this disclosure, a safety event may include but is not limited to: activities of a user of personal protective equipment (PPE), a condition of the PPE, or a hazardous environmental condition to name only a few examples. By training a safety learning model based on the training set, a safety learning model may be configured by PPEMS 6 to, when applying a particular feature vector to the safety learning model, generate higher probabilities or scores for safety events that correspond to training feature vectors that are more similar the particular feature set. In the same way, the safety learning model may be configured by PPEMS 6 to, when applying a particular feature vector to the safety learning model, generate lower probabilities or scores for safety events that correspond to training feature vectors that are less similar the particular feature set. Accordingly, the safety learning model may be trained, such that upon receiving a feature vector of metrics, the safety learning model may output one or more probabilities or scores that indicate likelihoods of safety events based on the feature vector. As such, PPEMS 6 may select likelihood of the occurrence as a highest likelihood of occurrence of a safety event in the set of likelihoods of safety events. In this way, as described above, the model may account for or otherwise take into account many different contexts and/or factors that may predict different safety events.

In some instances, PPEMS 6 may apply analytics techniques of this disclosure for combinations of PPE. For example, PPEMS 6 may identify correlations between users of SRLs 11 and/or the other PPE that is used with SRLs 11. That is, in some instances, PPEMS 6 may determine the likelihood of a safety event based not only on usage data from SRLs 11, but also from usage data from other PPE being used with SRLs 11. In such instances, PPEMS 6 may include one or more safety models that are constructed from data of known safety events from one or more devices other than SRLs 11 that are in use with SRLs 11.

According to aspects of this disclosure, while certain techniques of FIG. 1 are described with respect to PPEMS 6, in other examples, one or more functions may be implemented by SRL 11. For example, as shown in the example of FIG. 2, SRL includes usage data 120, models/rules 122, and alert engine 124. Usage data 120 may include data regarding operation of SRL 11, which may be indicative of activities of worker 10.

Models/rules 122 may include historical data and models, such as historical data and models 74B (FIG. 2). Models/rules 122 may also include selection rules for determining whether computing device 98 is responsible for processing usage data 120 (or whether such processing is performed by another component, such as hub 14 and/or PPEMS 6). The selection rules may include, as examples, any of the selection rules described with respect to selection rules 74H (FIG. 2).

Alert engine 124 may be a combination of hardware and software that is configured to apply usage data 120 to models/rules 122 in order to compute assertions, such as anomalies or predicted occurrences of imminent safety events based on environmental conditions or behavior patterns of a worker using SRL 11. Alert engine 124 may apply selection rules to determine whether processing of usage data is performed locally. In instances in which processing is performed locally, alert engine 124 may apply analytics to identify relationships or correlations between sensed data from SRL 11, environmental conditions of environment in which SRL 11 is located, a geographic region in which SRL 11 is located, and/or other factors. Alert engine 124 may determine, based on the data acquired across populations of workers 10, which particular activities, possibly within certain environment or geographic region, lead to, or are predicted to lead to, unusually high occurrences of safety events. Alert engine 124 may generate alert data based on the determinations for output by output unit 118 or transmission to another computing device.

Figure 4:
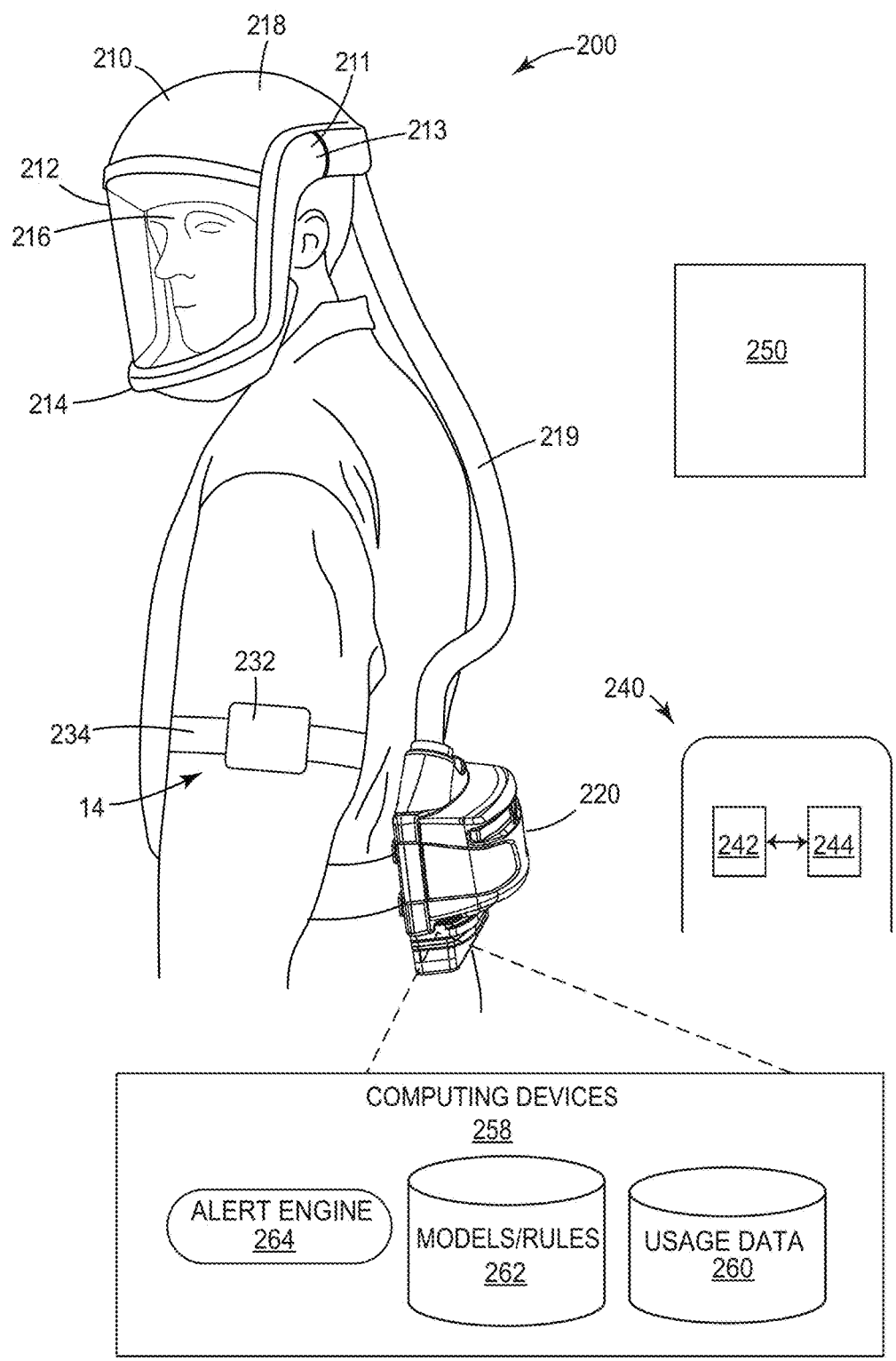
FIG. 4 is a conceptual diagram illustrating one example of a respirator, in accordance with aspects of this disclosure.

FIG. 4 is a system diagram of an exposure indicating supplied air respirator system 200. System 200 represents one example of respirators 13 shown in FIG. 2. System 200 includes head top 210, clean air supply source 220, hub 14, environmental beacon 240 and PPEMS 250 (which may be an example of PPEMS 6 of this disclosure). Head top 210 is connected to clean air supply source 220 by hose 219. Clean air supply source 220 can be any type of air supply source, such as a blower assembly for a powered air purifying respirator (PAPR), an air tank for a self-contained breathing apparatus (SCBA) or any other device that provides air to head top 210. In FIG. 3, clean air supply source 220 is a blower assembly for a PAPR. A PAPR is commonly used by individuals working in areas where there is known to be, or there is a potential of there being dusts, fumes or gases that are potentially harmful or hazardous to health. A PAPR typically includes a blower assembly, including a fan driven by an electric motor for delivering a forced flow of air to the respirator user. The air is passed from the PAPR blower assembly through hose 219 to the interior of head top 210.

Head top 210 includes a visor 212 that is sized to fit over at least a user's nose and mouth. Visor 212 includes lens 216 which is secured to helmet 218 by the frame assembly 214. Head top also includes a position sensor 211 that senses the position of visor 212 relative to helmet 218 to determine if the visor is in an open position or in a closed position. In some instances, position sensor 211 may detect whether visor 212 is partially open, and if so, what measure (e.g., percent or degree) it is open. As an example, the position sensor 210 may be a gyroscope that computes angular yaw, pitch, and/or roll (in degrees or radians) of the visor 212 relative to the helmet 218. In another example, the position sensor 210 may be a magnet. A percent may be estimated respecting how open a visor 212 is in relation to the helmet 218 by determining the magnetic field strength or flux perceived by the position sensor 210. "Partially open" visor information can be used to denote that the user may be receiving eye and face protection for hazards while still receiving a reasonable amount of respiratory protection. This "partially open" visor state, if kept to short durations, can assist the user in face to face communications with other workers. Position sensor 211 can be a variety of types of sensors, for example, an accelerometer, gyro, magnet, switch, potentiometer, digital positioning sensor or air pressure sensor. Position sensor 211 can also be a combination of any of the sensors listed above, or any other types of sensors that can be used to detected the position of the visor 212 relative to the helmet 218. Head top 210 may be supported on a user's head by a suspension (not shown).

Head top 210 may include other types of sensors. For example, head top 210 may include temperature sensor 213 that detects the ambient temperature in the interior of head top 210. Head top 210 may include other sensors such as an infrared head detection sensor positioned near the suspension of head top 210 to detect the presence of a head in head top 210, or in other words, to detect whether head top 210 is being worn at any given point in time. Head top 210 may also include other electronic components, such as a communication module, a power source, such as a battery, and a processing component. A communication module may include a variety of communication capabilities, such as radio frequency identification (RFID), Bluetooth, including any generations of Bluetooth, such as Bluetooth low energy (BLE), any type of wireless communication, such as WiFi, Zigbee, radio frequency or other types of communication methods as will be apparent to one of skill in the art up one reading the present disclosure.

Communication module in head top 210 can electronically interface with sensors, such as position sensor 211 or temperature sensor 213, such that it can transmit information from position sensor 211 or temperature sensor 213 to other electronic devices, including hub 14.

Hub 14 illustrates one example of hubs 14 shown in FIG. 2. Hub 14 includes a processor, a communication module and a power supply. The communication module of hub 14 can include any desired communication capability, such as: RFID, Bluetooth, including any generations of Bluetooth technology, and WiFi communication capabilities. Hub 14 can also include any type of wireless communication capabilities, such as radio frequency or Zigbee communication.

Hub 14 includes electronics module 232 that has a power source, such as a battery, to provide power to both the processor and communication module. A rechargeable battery, such as a Lithium Ion battery, can provide a compact and long-life source of power. Hub 14 may be adapted to have electrical contacts exposed or accessible from the exterior of the hub to allow recharging the hub 14.

Hub 14 can include a processor that can receive, store and process information. For example, communication module in hub 14 may receive information from a communication module in head top 210 or directly from the position sensor 211 indicating the position of visor 212, whether visor 212 is open or closed, and at what time the visor 212 position changed. Any information collected by sensors and transmitted to or from hub 14 can be time stamped based on the time of an event that was sensed or detected, based on the time of transmission of information, or both. Processor in hub 14 can store this information and compare it with other information received. Other information received may include, for example, information from environmental beacon 240 and information from PPEMS 250. Hub 14 can further store rules, such as threshold information both for a length of time visor 212 is allowed to be in an open position before an alert is generated, and the level or type of contaminants that will trigger an alert. For example, when hub 14 receives information from environmental beacon 240 that there are no hazards present in the environment, the threshold for the visor 212 being in the open position may be infinite. If a hazard is present in the environment, then the threshold would be determined based upon the concern of the threat to the user. Radiation, dangerous gases, or toxic fumes would all require assignment of the threshold to be on the order of one second or less. Thresholds for head top temperature can be used to predict heat related illness and more frequent hydration and/or rest periods can be recommended to the user. Thresholds can be used for predicted battery run time. As the battery nears selectable remaining run time, the user can be notified/warned to complete their current task and seek a fresh battery. When a threshold is exceed for a specific environmental hazard, an urgent alert can be given to the user to evacuate the immediate area. Thresholds can be customized to various levels of openness for the visor. In other words, a threshold for the amount of a time the visor may be open without triggering an alarm may be longer if the visor is in the partially open position as compared to the open position.

A user's individual state of health could be a factor for adjusting the threshold. If a user is in a situation where donning or doffing could take a long time, battery notification threshold could be adjusted to allow for time to don and doff PPE. Reaching different thresholds may result in triggering different types of alerts or alarms. For example, alarms may be informational (not requiring a user response), urgent (repeated and requiring a response or acknowledgement from a user), or emergency (requiring immediate action from a user.) The type of alert or alarm can be tailored to the environment. Different types of alerts and alarms can be coupled together to get user attention. In some instances, a user may be able to "snooze" an alert or alarm.

Hub 14 may include a user interface, such as a display, lights, buttons, keys (such as arrow or other indicator keys), and may be able to provide alerts to the user in a variety of ways, such as by sounding an alarm or vibrating. The user interface can be used for a variety of functions. For example, a user may be able to acknowledge or snooze an alert through the user interface. The user interface may also be used to control settings for the head top and/or turbo peripherals that are not immediately within the reach of the user. For example, the turbo may be worn on the lower back where the wearer cannot access the controls without significant difficulty.

Hub 14 can be portable such that it can be carried or worn by a user. Hub 14 can also be personal, such that it is used by an individual and communicates with personal protective equipment (PPE) assigned to that individual. In FIG. 4, hub 14 is secured to a user using a strap 234. However, communication hub may be carried by a user or secured to a user in other ways, such as being secured to PPE being worn by the user, to other garments being worn to a user, being attached to a belt, band, buckle, clip or other attachment mechanism as will be apparent to one of skill in the art upon reading the present disclosure.

Environmental beacon 240 includes at least environmental sensor 242 which detects the presence of a hazard and communication module 244. Environmental sensor 242 may detect a variety of types of information about the area surrounding environmental beacon 240. For example, environmental sensor 242 may be a thermometer detecting temperature, a barometer detecting pressure, an accelerometer detecting movement or change in position, an air contaminant sensor for detecting potential harmful gases like carbon monoxide, or for detecting air-born contaminants or particulates such as smoke, soot, dust, mold, pesticides, solvents (e.g., isocyanates, ammonia, bleach, etc.), and volatile organic compounds (e.g., acetone, glycol ethers, benzene, methylene chloride, etc.). Environmental sensor 242 may detect, for example any common gasses detected by a four gas sensor, including: CO, O2, HS and Low Exposure Limit. In some instances, environmental sensor 242 may determine the presence of a hazard when a contaminant level exceeds a designated hazard threshold. In some instances, the designated hazard threshold is configurable by the user or operator of the system. In some instances, the designated hazard threshold is stored on at least one of the environmental sensor and the personal communication hub. In some instances, the designated hazard threshold is stored on PPEMS 250 and can be sent to hub 14 or environmental beacon 240 and stored locally on hub 14 or environmental beacon 240.

Environmental beacon communication module 244 is electronically connected to environmental sensor 242 to receive information from environmental sensor 242. Communication module 244 may include a variety of communication capabilities, such as: RFID, Bluetooth, including any generations of Bluetooth technology, and WiFi communication capabilities. Hub 14 can also include any type of wireless communication capabilities, such as radio frequency or Zigbee communication.

In some instances, environmental beacon 240 may store hazard information based on the location of environmental beacon 240. For example, if environmental beacon 240 is in an environment known to have physical hazards, such as the potential of flying objects, environmental beacon 240 may store such information and communicate the presence of a hazard based on the location of environmental beacon 240. In other instances, the signal indicating the presence of a hazard may be generated by environmental beacon 240 based on detection of a hazard by environmental sensor 242.

The system may also have an exposure threshold. An exposure threshold can be stored on any combination of PPEMS 250, hub 14, environmental beacon 240, and head top 210. A designated exposure threshold is the time threshold during which a visor 212 can be in the open position before an alert is generated. In other words, if the visor is in the open position for a period of time exceeding a designated exposure threshold, an alert may be generated. The designated exposure threshold may be configurable by a user or operator of the system. The designated exposure threshold may depend on personal factors related to the individual's health, age, or other demographic information, on the type of environment the user is in, and on the danger of the exposure to the hazard.

An alert can be generated in a variety of scenarios and in a variety of ways. For example, the alert may be generated by the hub 14 based on information received from head top 210 and environmental sensor 140. An alert may be in the form of an electronic signal transmitted to PPEMS 250 or to any other component of system 200. An alert may comprise one or more of the following types of signals: tactile, vibration, audible, visual, heads-up display or radio frequency signal.

According to aspects of this disclosure, computing device 258 may be configured to process usage data to detect a safety event signatures. For example, computing device 258 includes usage data 260, models/rules 262, and alert engine 264. Usage data 260 may include data regarding operation of system 200, which may be indicative of activities of worker 10. Models/rules 262 may include historical data and models, such as historical data and models 74B (FIG. 2). Models/rules 262 may also include selection rules for determining whether computing device 98 is responsible for processing usage data 120 (or whether such processing is performed by another component, such as hub 14 and/or PPEMS 6). The selection rules may include, as examples, any of the selection rules described with respect to selection rules 74H (FIG. 2).

Alert engine 264 may be a combination of hardware and software that is configured to apply usage data 260 to models/rules 262 in order to compute assertions, such as identifying safety event signatures, anomalies or predicted occurrences of imminent safety events based on environmental conditions or behavior patterns of a worker using system 200. Alert engine 264 may apply selection rules to determine whether processing of usage data is performed locally. In instances in which processing is performed locally, alert engine 264 may process usage data 260 to identify relationships or correlations between sensed data from system 200, environmental conditions of environment in which system 200 is located, a geographic region in which system 200 is located, and/or other factors. Alert engine 264 may determine, based on the data acquired across populations of workers 10, which particular activities, possibly within certain environment or geographic region, lead to, or are predicted to lead to, unusually high occurrences of safety events. Alert engine 264 may generate alert data based on the determinations for output or transmission to another computing device.

Figure 5:
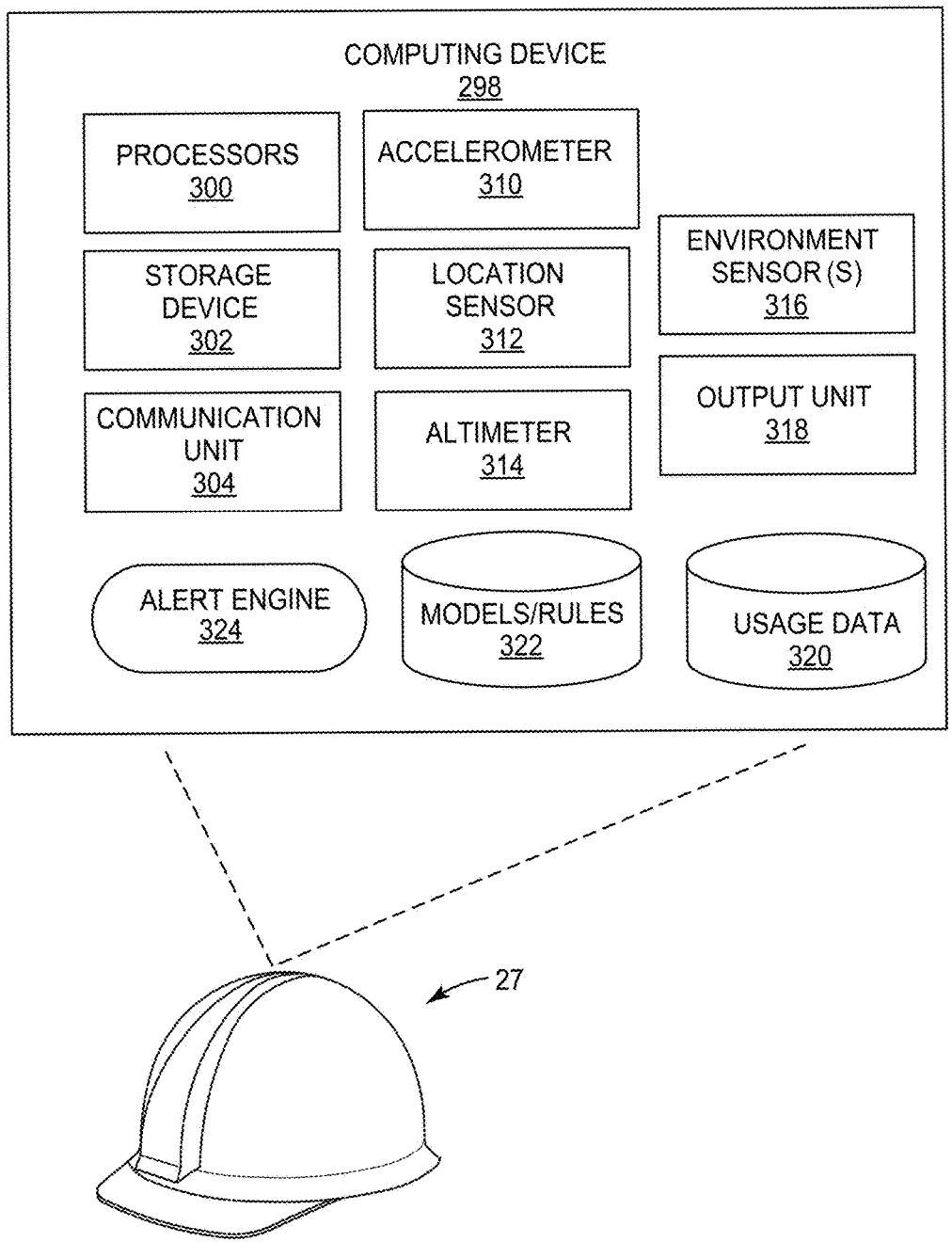
FIG. 5 is a conceptual diagram illustrating one example of head protection, in accordance with aspects of this disclosure.

FIG. 5 illustrates an example of one of head protection 27 in greater detail. Head protection 27 computing device 298 includes processors 300, storage device 302, communication unit 304, an accelerometer 310, a location sensor 312, an altimeter 314, one or more environment sensors 316, output unit 318, usage data 320, models/rules 322, and alert engine 324.

It should be understood that the architecture and arrangement of computing device 298 illustrated in FIG. 5 is shown for exemplary purposes only. In other examples, head protection 27 and computing device 298 may be configured in a variety of other ways having additional, fewer, or alternative components than those shown in FIG. 3. For example, in some instances, computing device 298 may be configured to include only a subset of components, such as communication unit 104 and accelerometer 310. Moreover, although FIGS. 3-5 illustrate various specific types of PPE for illustration, the techniques of this disclosure may be applied to any type of PPE.

In general, computing device 298 may include a plurality of sensors that may capture real-time data regarding operation of head protection 27 and/or an environment in which head protection 27 is used. Such data may be referred to herein as usage data. Processors 300, in one example, are configured to implement functionality and/or process instructions for execution within computing device 298. For example, processors 300 may be capable of processing instructions stored by storage device 102. Processors 300 may include, for example, microprocessors, digital signal processors (DSPs), application specific integrated circuits (ASICs), field-programmable gate array (FPGAs), or equivalent discrete or integrated logic circuitry.

Storage device 302 may include a computer-readable storage medium or computer-readable storage device. In some examples, storage device 302 may include one or more of a short-term memory or a long-term memory. Storage device 302 may include, for example, random access memories (RAM), dynamic random access memories (DRAM), static random access memories (SRAM), magnetic hard discs, optical discs, flash memories, or forms of electrically programmable memories (EPROM) or electrically erasable and programmable memories (EEPROM).

In some examples, storage device 302 may store an operating system (not shown) or other application that controls the operation of components of computing device 298. For example, the operating system may facilitate the communication of data from electronic sensors to communication unit 304. In some examples, storage device 302 is used to store program instructions for execution by processors 300. Storage device 302 may also be configured to store information within computing device 298 during operation.

Computing device 298 may use communication unit 304 to communicate with external devices via one or more wired or wireless connections. Communication unit 304 may include various mixers, filters, amplifiers and other components designed for signal modulation, as well as one or more antennas and/or other components designed for transmitting and receiving data. Communication unit 304 may send and receive data to other computing devices using any one or more suitable data communication techniques. Examples of such communication techniques may include TCP/IP, Ethernet, Wi-Fi, Bluetooth, 4G, LTE, to name only a few examples. In some instances, communication unit 104 may operate in accordance with the Bluetooth Low Energy (BLU) protocol.

Accelerometer 310 may be configured to generate data indicative of an acceleration of head protection 27 with respect to gravity. Accelerometer 310 may be configured as a single- or multi-axis accelerometer to determine a magnitude and direction of acceleration, e.g., as a vector quantity, and may be used to determine orientation, coordinate acceleration, vibration, shock, and/or falling. Location sensor 312 may be configured to generate data indicative of a location of head protection 27 in one of environments 8. Location sensor 312 may include a Global Positioning System (GPS) receiver, componentry to perform triangulation (e.g., using beacons and/or other fixed communication points), or other sensors to determine the relative location of head protection 27. Altimeter 314 may be configured to generate data indicative of an altitude of head protection 27 above a fixed level. In some examples, altimeter 314 may be configured to determine altitude of head protection 27 based on a measurement of atmospheric pressure (e.g., the greater the altitude, the lower the pressure).

Environment sensors 316 may be configured to generate data indicative of a characteristic of an environment, such as environments 8. In some examples, environment sensors 316 may include one or more sensors configured to measure temperature, humidity, particulate content, noise levels, air quality, or any variety of other characteristics of environments in which head protection 27 may be used.

Output unit 318 may be configured to output data that is indicative of operation of head protection 27, e.g., as measured by one or more sensors of head protection 27 (e.g., such as accelerometer 310, location sensor 312, altimeter 314, and/or environmental sensors 316). Output unit 318 may include instructions executable by processors 300 of computing device 298 to generate the data associated with operation of head protection 27. In some examples, output unit 318 may directly output the data from the one or more sensors of head protection 27. For example, output unit 318 may generate one or more messages containing real-time or near real-time data from one or more sensors of head protection 27 for transmission to another device via communication unit 304.

In some examples, output unit 318 may be configured to transmit the usage data in real-time or near-real time to another device (e.g., PPE 62) via communication unit 304. However, in some instances, communication unit 304 may not be able to communicate with such devices, e.g., due to an environment in which head protection 27 is located and/or network outages. In such instances, output unit 318 may cache usage data to storage device 302. That is, output unit 318 (or the sensors themselves) may store usage data to storage device 302, e.g., as usage data 320, which may allow the usage data to be uploaded to another device upon a network connection becoming available.

Output unit 318 may also be configured to generate an audible, visual, tactile, or other output that is perceptible by a user of head protection 27. For example, output unit 318 may include one more user interface devices including, as examples, a variety of lights, displays, haptic feedback generators, speakers or the like.

Output unit 318 may interpret received alert data and generate an output (e.g., an audible, visual, or tactile output) to notify a worker using head protection 27 of an alert condition (e.g., that the likelihood of a safety event is relatively high, that the environment is dangerous, that head protection 27 is malfunctioning, that one or more components of head protection 27 need to be repaired or replaced, or the like).

According to aspects of this disclosure, usage data from sensors of head protection 27 (e.g., data from accelerometer 310, location sensor 312, altimeter 314, environmental sensors 116, or other sensors) may be used in a variety of ways. For example, PPEMS 6 may determine performance characteristics and/or generate the alert data based on application of usage data to one or more safety models that characterizes activity of a user of head protection 27. The safety models may be trained based on historical data or known safety events. However, while the determinations are described with respect to PPEMS 6, as described in greater detail herein, one or more other computing devices, such as hubs 14 or head protection 27 may be configured to perform all or a subset of such functionality.

For example, as shown in the example of FIG. 5, head protection 27 includes usage data 320, models/rules 322, and alert engine 324. Usage data 320 may include data regarding operation of head protection 27, which may be indicative of activities of worker 10. Models/rules 322 may include historical data and models, such as historical data and models 74B (FIG. 2). Models/rules 322 may also include selection rules for determining whether computing device 258 is responsible for processing usage data 320 (or whether such processing is performed by another component, such as hub 14 and/or PPEMS 6). The selection rules may include, as examples, any of the selection rules described with respect to selection rules 74H (FIG. 2).

Alert engine 324 may be a combination of hardware and software that is configured to apply usage data 320 to models/rules 322 in order to compute assertions, such as identifying safety event signatures, anomalies or predicted occurrences of imminent safety events based on environmental conditions or behavior patterns of a worker using head protection 27. Alert engine 324 may apply selection rules to determine whether processing of usage data is performed locally. In instances in which processing is performed locally, alert engine 324 may process streams of usage data to identify relationships or correlations between sensed data from head protection 27, environmental conditions of environment in which head protection 27 is located, a geographic region in which head protection 27 is located, and/or other factors. Alert engine 324 may determine, based on the data acquired across populations of workers 10, which particular activities, possibly within certain environment or geographic region, lead to, or are predicted to lead to, unusually high occurrences of safety events. Alert engine 324 may generate alert data based on the determinations for output or transmission to another computing device.

Figure 6:
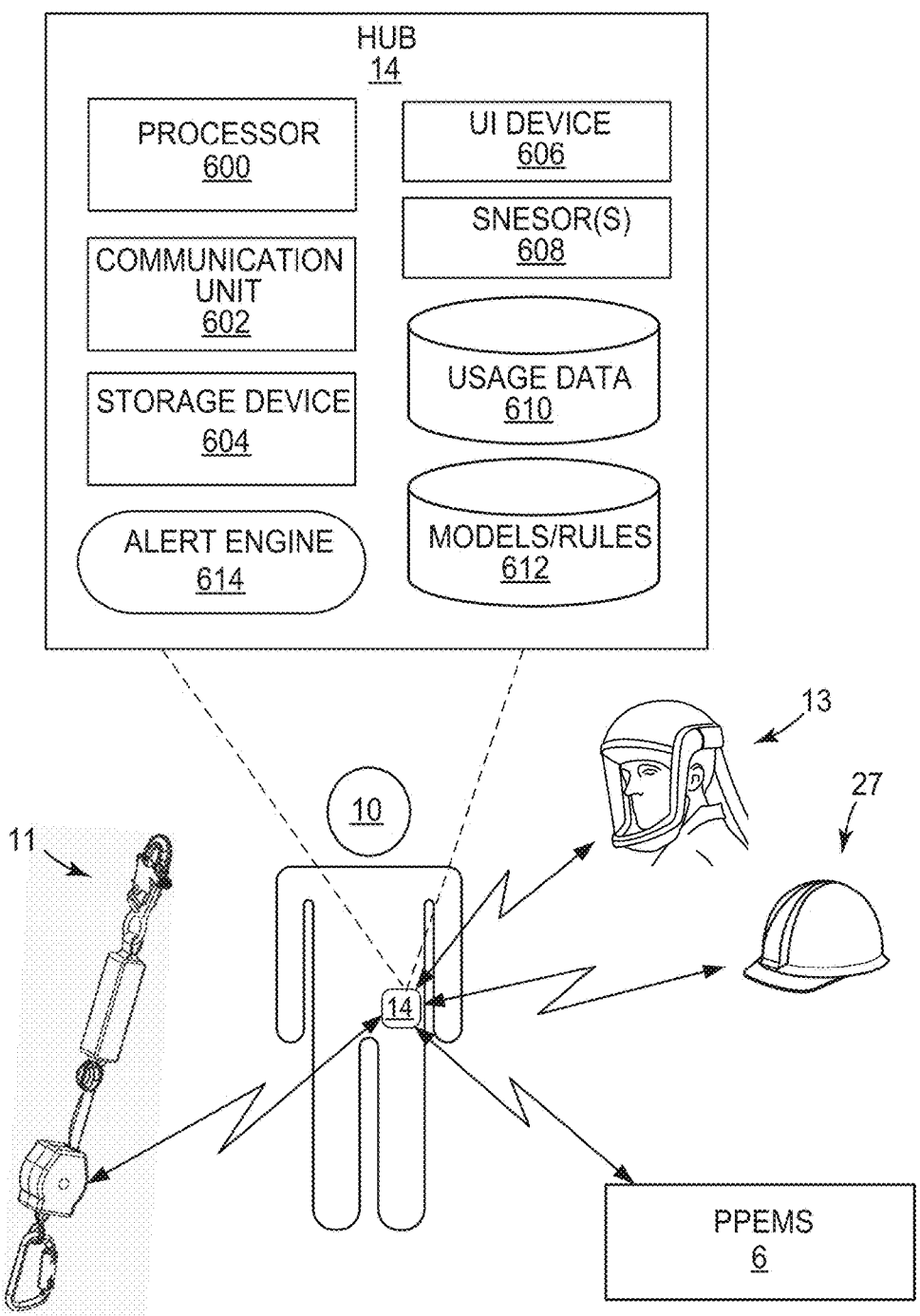
FIG. 6 is a conceptual diagram illustrating an example of PPE in communication with a wearable data hub, in accordance with various aspects of this disclosure.

FIG. 6 illustrates components of hub 14 including processor 600, communication unit 602, storage device 604, user-interface (UI) device 606, sensors 608, usage data 610, models/rules 612, and alert engine 614. As noted above, hub 14 represents one example of hubs 14 shown in FIG. 2. FIG. 6 illustrates only one particular example of hub 14, as shown in FIG. 6. Many other examples of hub 14 may be used in other instances and may include a subset of the components included in example hub 14 or may include additional components not shown example hub 14 in FIG. 6.

In some examples, hub 14 may be an intrinsically safe computing device, smartphone, wrist- or head-worn computing device, or any other computing device that may include a set, subset, or superset of functionality or components as shown in hub 14. Communication channels may interconnect each of the components in hub 14 for inter-component communications (physically, communicatively, and/or operatively). In some examples, communication channels may include a hardware bus, a network connection, one or more inter-process communication data structures, or any other components for communicating data between hardware and/or software.

Hub 14 may also include a power source, such as a battery, to provide power to components shown in hub 14. A rechargeable battery, such as a Lithium Ion battery, can provide a compact and long-life source of power. Hub 14 may be adapted to have electrical contacts exposed or accessible from the exterior of the hub to allow recharging the hub 14. As noted above, hub 14 may be portable such that it can be carried or worn by a user. Hub 14 can also be personal, such that it is used by an individual and communicates with personal protective equipment (PPE) assigned to that individual. However, communication hub may be carried by a user or secured to a user in other ways, such as being secured to PPE being worn by the user, to other garments being worn to a user, being attached to a belt, band, buckle, clip or other attachment mechanism as will be apparent to one of skill in the art upon reading the present disclosure.

One or more processors 600 may implement functionality and/or execute instructions within hub 14. For example, processor 600 may receive and execute instructions stored by storage device 604. These instructions executed by processor 600 may cause hub 14 to store and/or modify information, within storage devices 604 during program execution. Processors 600 may execute instructions of components, such as alert engine 614 to perform one or more operations in accordance with techniques of this disclosure. That is, alert engine 614 may be operable by processor 600 to perform various functions described herein.

One or more communication units 602 of hub 14 may communicate with external devices by transmitting and/or receiving data. For example, hub 14 may use communication units 602 to transmit and/or receive radio signals on a radio network such as a cellular radio network. In some examples, communication units 602 may transmit and/or receive satellite signals on a satellite network such as a Global Positioning System (GPS) network. Examples of communication units 602 include a network interface card (e.g. such as an Ethernet card), an optical transceiver, a radio frequency transceiver, a GPS receiver, or any other type of device that can send and/or receive information. Other examples of communication units 602 may include Bluetooth®, GPS, 3G, 4G, and Wi-Fi® radios found in mobile devices as well as Universal Serial Bus (USB) controllers and the like.

One or more storage devices 604 within hub 14 may store information for processing during operation of hub 14. In some examples, storage device 604 is a temporary memory, meaning that a primary purpose of storage device 604 is not long-term storage. Storage device 604 may be configured for short-term storage of information as volatile memory and therefore not retain stored contents if deactivated. Examples of volatile memories include random access memories (RAM), dynamic random access memories (DRAM), static random access memories (SRAM), and other forms of volatile memories known in the art.

Storage device 604 may, in some examples, also include one or more computer-readable storage media. Storage device 604 may be configured to store larger amounts of information than volatile memory. Storage device 604 may further be configured for long-term storage of information as non-volatile memory space and retain information after activate/off cycles. Examples of non-volatile memories include magnetic hard discs, optical discs, floppy discs, flash memories, or forms of electrically programmable memories (EPROM) or electrically erasable and programmable (EEPROM) memories. Storage device 604 may store program instructions and/or data associated with components such as alert engine 614.

UI device 606 may be configured to receive user input and/or output information to a user. One or more input components of UI device 606 may receive input. Examples of input are tactile, audio, kinetic, and optical input, to name only a few examples. UI device 606 of hub 14, in one example, include a mouse, keyboard, voice responsive system, video camera, buttons, control pad, microphone or any other type of device for detecting input from a human or machine. In some examples, UI device 606 may be a presence-sensitive input component, which may include a presence-sensitive screen, touch-sensitive screen, etc.

One or more output components of UI device 606 may generate output. Examples of output are data, tactile, audio, and video output. Output components of UI device 606, in some examples, include a presence-sensitive screen, sound card, video graphics adapter card, speaker, cathode ray tube (CRT) monitor, liquid crystal display (LCD), or any other type of device for generating output to a human or machine. Output components may include display components such as cathode ray tube (CRT) monitor, liquid crystal display (LCD), Light-Emitting Diode (LED) or any other type of device for generating tactile, audio, and/or visual output. Output components may be integrated with hub 14 in some examples.

UI device 606 may include a display, lights, buttons, keys (such as arrow or other indicator keys), and may be able to provide alerts to the user in a variety of ways, such as by sounding an alarm or vibrating. The user interface can be used for a variety of functions. For example, a user may be able to acknowledge or snooze an alert through the user interface. The user interface may also be used to control settings for the head top and/or turbo peripherals that are not immediately within the reach of the user. For example, the turbo may be worn on the lower back where the wearer cannot access the controls without significant difficulty.

Sensors 608 may include one or more sensors that generate data indicative of an activity of a worker 10 associated with hub 14 and/or data indicative of an environment in which hub 14 is located. Sensors 608 may include, as examples, one or more accelerometers, one or more sensors to detect conditions present in a particular environment (e.g., sensors for measuring temperature, humidity, particulate content, noise levels, air quality, or any variety of other characteristics of environments in which respirator 13 may be used), or a variety of other sensors.

Hub 14 may store usage data 610 from PPE, such as SRLs 11, respirators 13, head protection 27, or the like. Usage data 610 may include data regarding operation of the PPE, which may be indicative of activities of worker 10. Models/rules 612 may include historical data and models, such as historical data and models 74B (FIG. 2). For example, in some instances, hub 14 may have processing capabilities that allows hub 14 to process streams of sensor data locally.

In such examples, hub 14 may apply usage data 610 of PPEs to models/rules 612. Models/rules 612 may include historical data and models, such as historical data and models 74B (FIG. 2). Models/rules 612 may also include selection rules for determining whether hub 14 is responsible for processing usage data 610 (or whether such processing is performed by another component, such as PPE 62 and/or PPEMS 6). The selection rules may include, as examples, any of the selection rules described with respect to selection rules 74H (FIG. 2).

Alert engine 614 may be a combination of hardware and software that is configured to apply usage data 610 to models/rules 612 in order to compute assertions, such as identifying safety event signatures, anomalies or predicted occurrences of imminent safety events based on environmental conditions or behavior patterns of a worker using hub 14. Alert engine 614 may apply selection rules to determine whether processing of usage data is performed locally.

Figure 7:
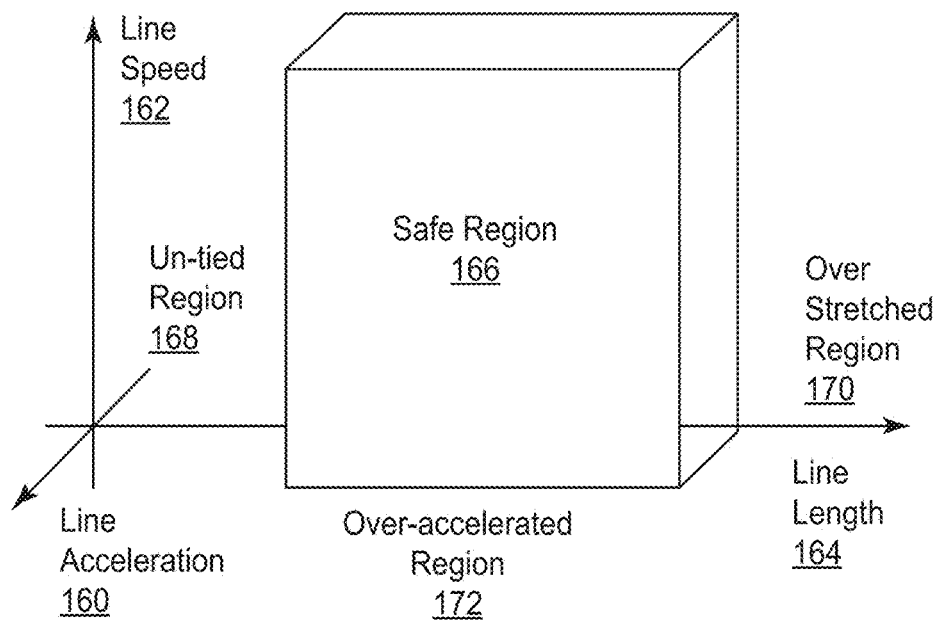
FIG. 7 is a graph that illustrates an example model applied by the personal protection equipment management system or other devices herein with respect to worker activity in terms of measure line speed, acceleration and line length, where the model is arranged to define safe regions and regions unsafe behavior predictive of safety events, in accordance with aspects of this disclosure.

FIG. 7 is a graph that illustrates an example model applied by the personal protection equipment management system or other devices herein with respect to worker activity in terms of measure line speed, acceleration and line length, where the model is arranged to define safe regions and regions unsafe. In other words, FIG. 7 is a graph representative of a model to which usage data is applied by PPEMS 6, hubs 14 or SRLs 11 to identify a safety event signature and/or predict the likelihood of a safety event associated with the safety event signature based on measurements of acceleration 160 of a lifeline (such as lifeline 92 shown in FIG. 3) being extracted, speed 162 of a lifeline 92 being extracted, and length 164 of a lifeline that has been extracted. The measurements of acceleration 160, speed 162, and length 164 may be determined based on data collected from sensors of SRLs 11. Data represented by the graph may be estimated or collected in a training/test environment and the graph may be used as a "map" to distinguish safe activities of a worker from unsafe activities.

While described with respect to one of SRLs 11, it should be understood that similar models may be developed for a variety of other PPE (such as respirators 13, head protection 27, hearing protection, or the like). As described herein, such models may be stored to PPEMS 6, hubs 14, and/or PPE 62 and used to identify a condition of the PPE.

In the example of FIG. 7, safe region 166 may represent measurements of acceleration 160, speed 162, and length 164 that are associated with safe activities (e.g., as determined by monitoring activities of a worker in a test environment). Untied region 168 may represent measurements of acceleration 160, speed 162, and length 164 that are associated with a lifeline that is not securely anchored to a support structure, which may be considered unsafe. Over stretched region 170 may represent measurements of acceleration 160, speed 162, and length 164 that are associated with a lifeline that is extended beyond normal operating parameters, which may also be considered unsafe.

According to aspects of this disclosure, PPEMS 6, hubs 14, or SRLs 11 may issue one or more alerts by applying usage data received from SRLs 11 to a model or rule set represented by FIG. 7. For example, PPEMS 6, hubs 14, or SRLs 11 may issue an alert if a stream of usage data such as measurements of acceleration 160, speed 162, or length 164 are outside of safe region 166. In some instances, different alerts may be issued based how far measurements of acceleration 160, speed 162, or length 164 are outside of safe region 166. In some examples, the determinations may compare a portion of a stream of use data from a predefined period of time to the model which may generate likelihoods of one or more safety event signatures that may correspond to safety events. If, for example, measurements of acceleration 160, speed 162, or length 164 are relatively close to safe region 166, PPEMS 6, hubs 14, or SRLs 11 may issue a warning that the activity is of concern and may result in a safety event. In another example, if measurements of acceleration 160, speed 162, or length 164 are relatively far from safe region 166, PPEMS 6, hubs 14, or SRLs 11 may issue a warning that the activity is unsafe and has a high likelihood of an immediate safety event.

In some instances, the data of the graph shown in FIG. 7 may be representative of historical data and models 74B shown in FIG. 2. In this example, PPEMS 6 may compare incoming streams of data to the model shown in FIG. 7 to determine a likelihood of a safety event. In other instances, a similar model may additionally or alternatively be stored to SRLs 11, respirators 13, head protection 27, and/or hubs 14, and alerts may be issued based on the locally stored data.

While the example of FIG. 7 illustrates acceleration 160, speed 162, and length 164, other models have more or fewer variables than those shown may be developed. In one example, a model may be generated based only on a length of a lifeline. In this example, an alert may be issued to a worker when the lifeline is extended beyond a line length specified by the model.

Figure 8:
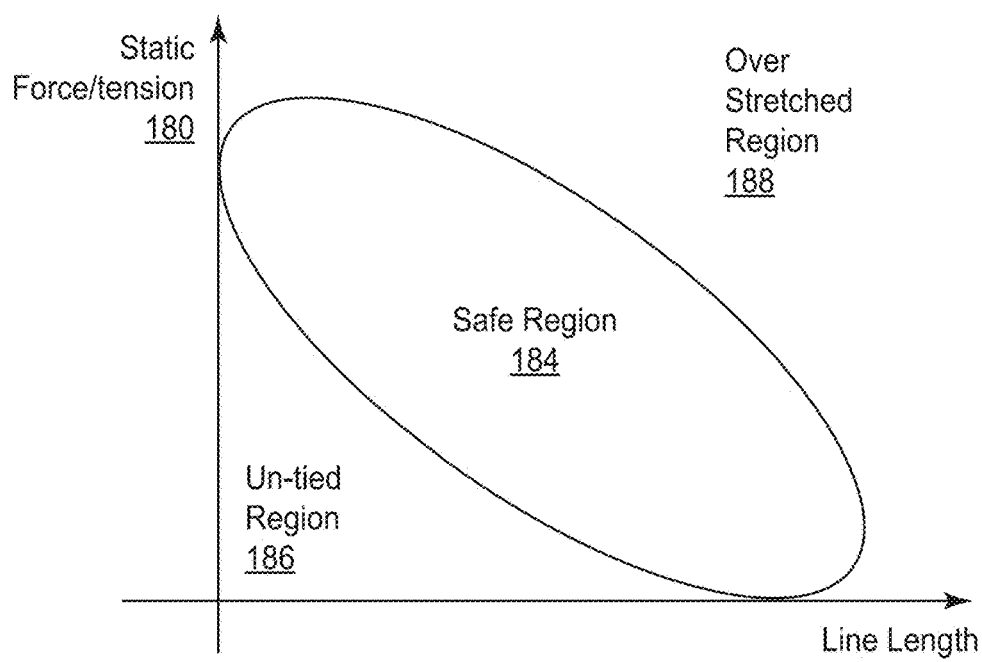
FIG. 8 is another a graph that illustrates an example of a second model applied by the personal protection equipment management system or other devices herein with respect to worker activity in terms of measure force/tension on the safety line and length, where the model is arranged to define a safe region and regions unsafe behavior predictive of safety events, in accordance with aspects of this disclosure.

FIG. 8 is another a graph that illustrates an example of a second model to which streams of usage data are applied by the personal protection equipment management system or other devices herein with respect to worker activity in terms of measure force/tension on the safety line and length, where the model is arranged to define a safe region and regions unsafe behavior predictive of safety events, in accordance with aspects of this disclosure. In this example, FIG. 8 is a graph representative of a model or ruleset to which streams of usage data are applied by PPEMS 6, hubs 14 or SRLs 11 to predict the likelihood of a safety event signature that corresponds to a safety event based on measurements of force or tension 180 on a lifeline (such as lifeline 92 shown in FIG. 3) and length 182 of a lifeline that has been extracted. The measurements of force or tension 180 and length 182 may be determined based on data collected from sensors of SRLs 11. Data represented by the graph may be estimated or collected in a training/test environment and the graph may be used as a "map" or model to distinguish safe activities of a worker from unsafe activities.

Again, while described with respect to one of SRLs 11, it should be understood that similar models may be developed for a variety of other PPE (such as respirators 13, head protection 27, hearing protection, or the like). As described herein, such models may be stored to PPEMS 6, hubs 14, and/or PPE 62 and used to identify a condition of the PPE.

For example, safe region 184 may represent measurements of force or tension 180 and length 182 that are associated with safe activities (e.g., as determined by monitoring activities of a worker in a test environment). Untied region 186 may represent measurements of force or tension 180 and length 182 that are associated with a lifeline that is not securely anchored to a support structure, which may be considered unsafe. Over stretched region 188 may represent measurements of force or tension 180 and length 182 that are associated with a lifeline that is extended beyond normal operating parameters, which may also be considered unsafe.

According to aspects of this disclosure, PPEMS 6, hubs 14, or SRLs 11 may issue one or more alerts by applying usage data from SRLs 11 to a model or rule set represented by FIG. 8, in a manner similar to that described above with respect to FIG. 8. In some instances, the data of the graph shown in FIG. 8 may be representative of historical data and models 74B shown in FIG. 2. In other instances, a similar map may additionally or alternatively be stored to SRLs 11 and/or hubs 14, and alerts may be issued based on the locally stored data.

Figure 9A:
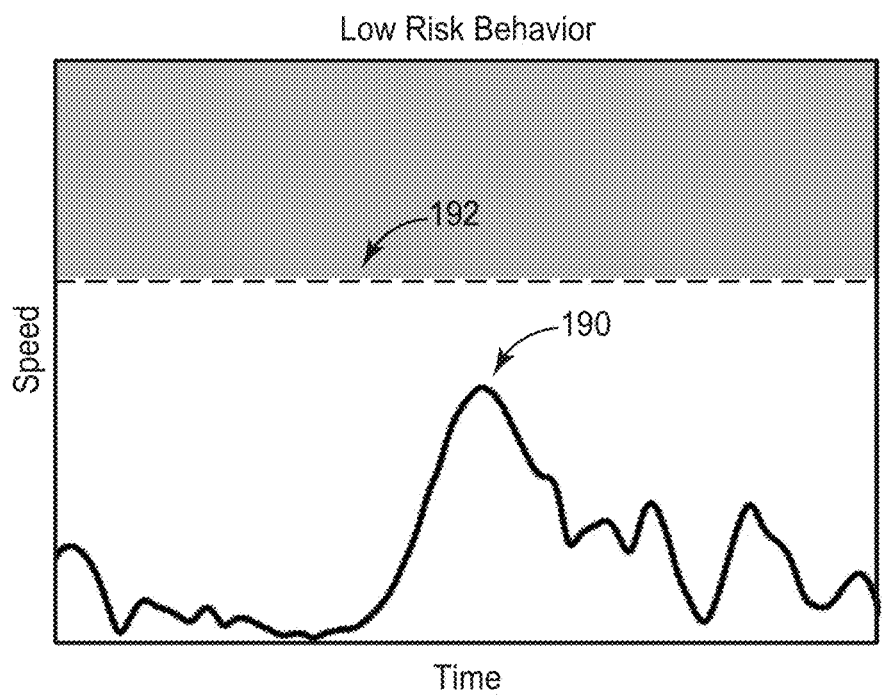
FIGS. 9A and 9B are graphs that illustrate profiles of example usage data from workers determined by the personal protection equipment management system to represent low risk behavior and high risk behavior triggering alerts or other responses, in accordance with aspects of this disclosure.
Figure 9B:
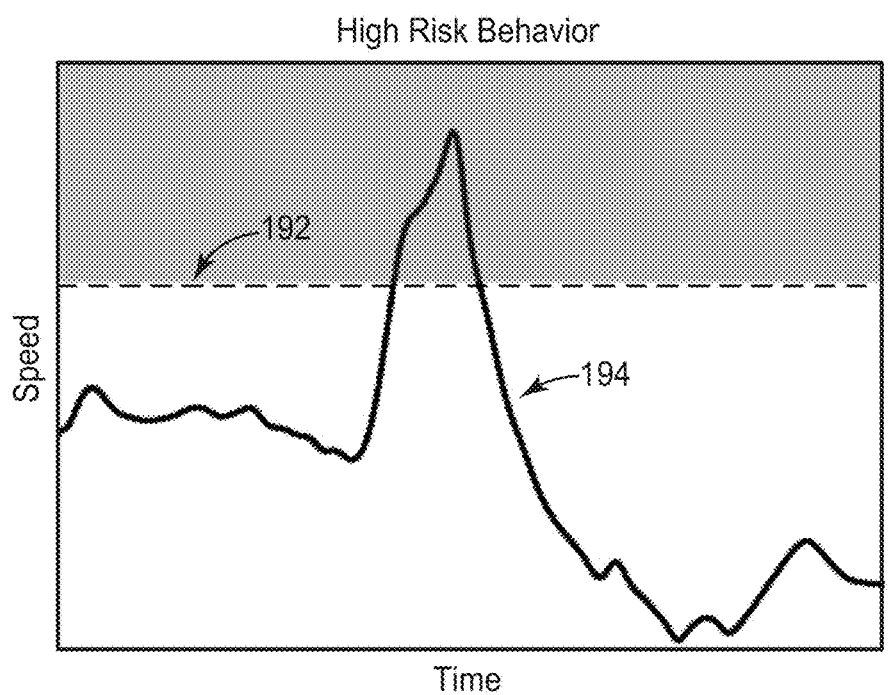

FIGS. 9A and 9B are graphs that illustrate profiles of example input streams of event data (e.g., usage data) received and processed by PPEMS 6, hubs 14 or SRLs 11 and, based on application of the event data to one or more models or rules sets, determined to represent low risk behavior (FIG. 9A) and high risk behavior (FIG. 9B), which results in triggering of alerts or other responses, in accordance with aspects of this disclosure. In the examples, FIGS. 9A and 9B illustrate profiles of example event data determined to indicate safe activity and unsafe activity, respectively, over a period of time. For example, the example of FIG. 9A illustrates a speed 190 with which a lifeline (such as lifeline 92 shown in FIG. 3) is extracted relative to a kinematic threshold 192, while the example of FIG. 9B illustrates a speed 194 with which a lifeline (such as lifeline 92 shown in FIG. 3) is extracted relative to threshold 192.

Again, while described with respect to one of SRLs 11, it should be understood that similar models may be developed for a variety of other PPE (such as respirators 13, head protection 27, hearing protection, or the like). As described herein, such models may be stored to PPEMS 6, hubs 14, and/or PPE 62 and used to identify a condition of the PPE. That is, in some instances, the profiles shown in FIGS. 8A and 8B may be developed and stored as historical data and models 74B of PPEMS 6 shown in FIG. 2. According to aspects of this disclosure, PPEMS 6, hubs 14, or SRLs 11 may issue one or more alerts by comparing a stream of usage data from SRLs 11 to threshold 192. For example, PPEMS 6, hubs 14, or SRLs 11 may issue one or more alerts when speed 194 exceeds threshold 192 in the example of FIG. 8B. In some instances, different alerts may be issued based how much the speed exceeds threshold 192, e.g., to distinguish risky activities from activity is unsafe and has a high likelihood of an immediate safety event.

FIGS. 10-13 illustrate various user interfaces that may be generated by PPEMS 6 in accordance with techniques of this disclosure. In some examples, PPEMS 6 may automatically reconfigure a user interface in response to identifying a safety event signature and/or detecting a safety event. For instance, PPEMS 6 may determine one or more characteristics of the safety event relating to PPE, worker, and/or worker environment associated with the event and update one or more user interfaces that include input controls customized to the particular safety event. For instance, specific details relating to the characteristics of the safety event such as PPE type, work environment location, and/or worker metrics may be presented in a user interface in response to the safety event to enable one or more persons to respond efficiently to the safety event with the relevant information.

FIGS. 10-13 illustrate example user interfaces (UIs) for representing usage data from one or more articles of PPE, according to aspects of this disclosure. For example, as described herein, respirators 13 may be configured to transmit acquired usage data to PPEMS 6. Computing devices, such as computing devices 60 may request PPEMS 6 to perform a database query to view acquired safety information, compliance information and any results of the analytic engine, e.g., by the way of dashboards, alert notifications, reports and the like. That is, as described herein, users 24, 26, or software executing on computing devices 16, 18, (FIG. 1) may submit queries to PPEMS 6 and receive data corresponding to the queries for presentation in the form of one or more reports or dashboards. The UIs shown in FIGS. 10-13 represent examples of such reports or dashboards, and may be output, for example, at any of computing devices 60 (FIG. 2).

Figure 10:
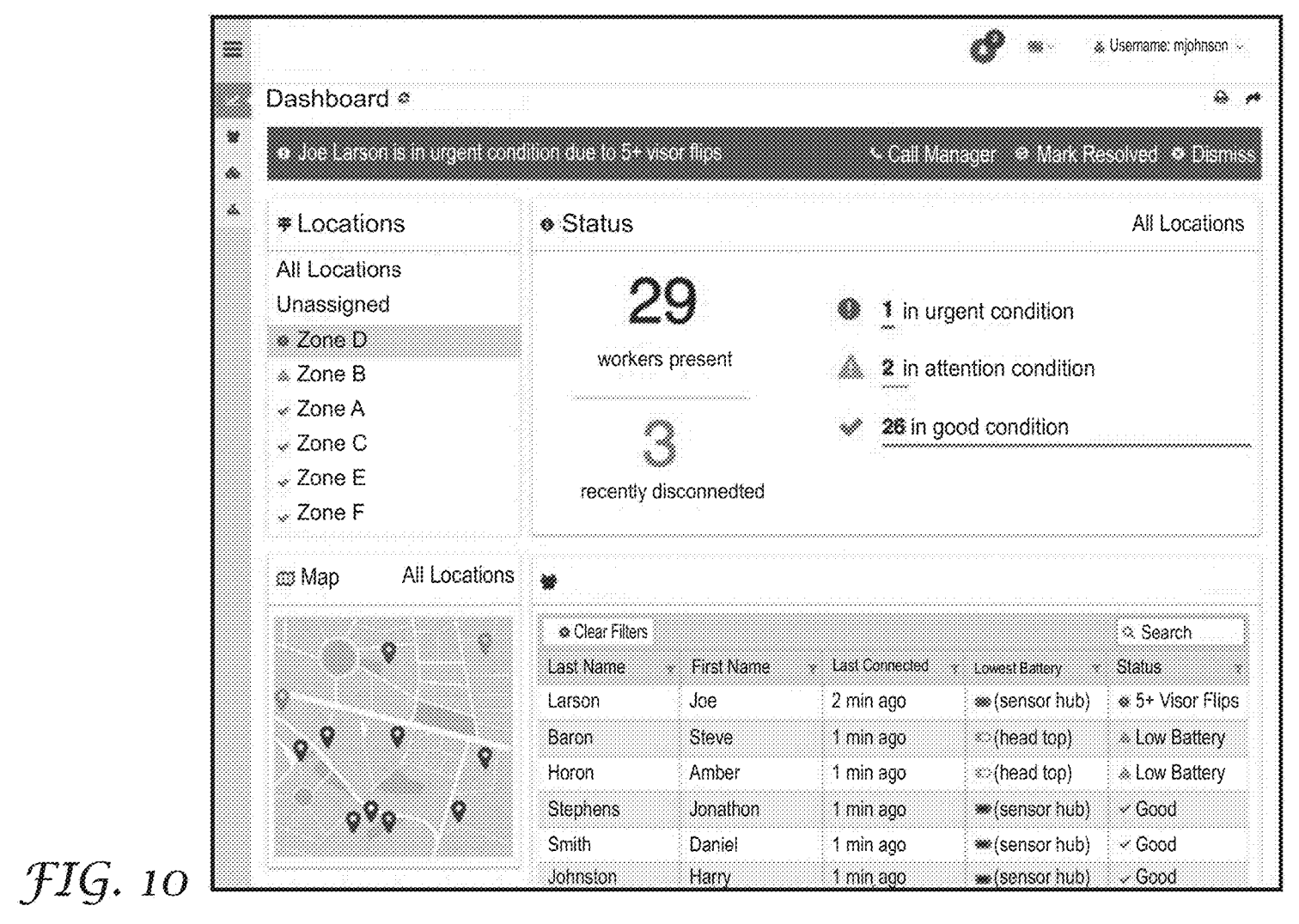
Figure 11:
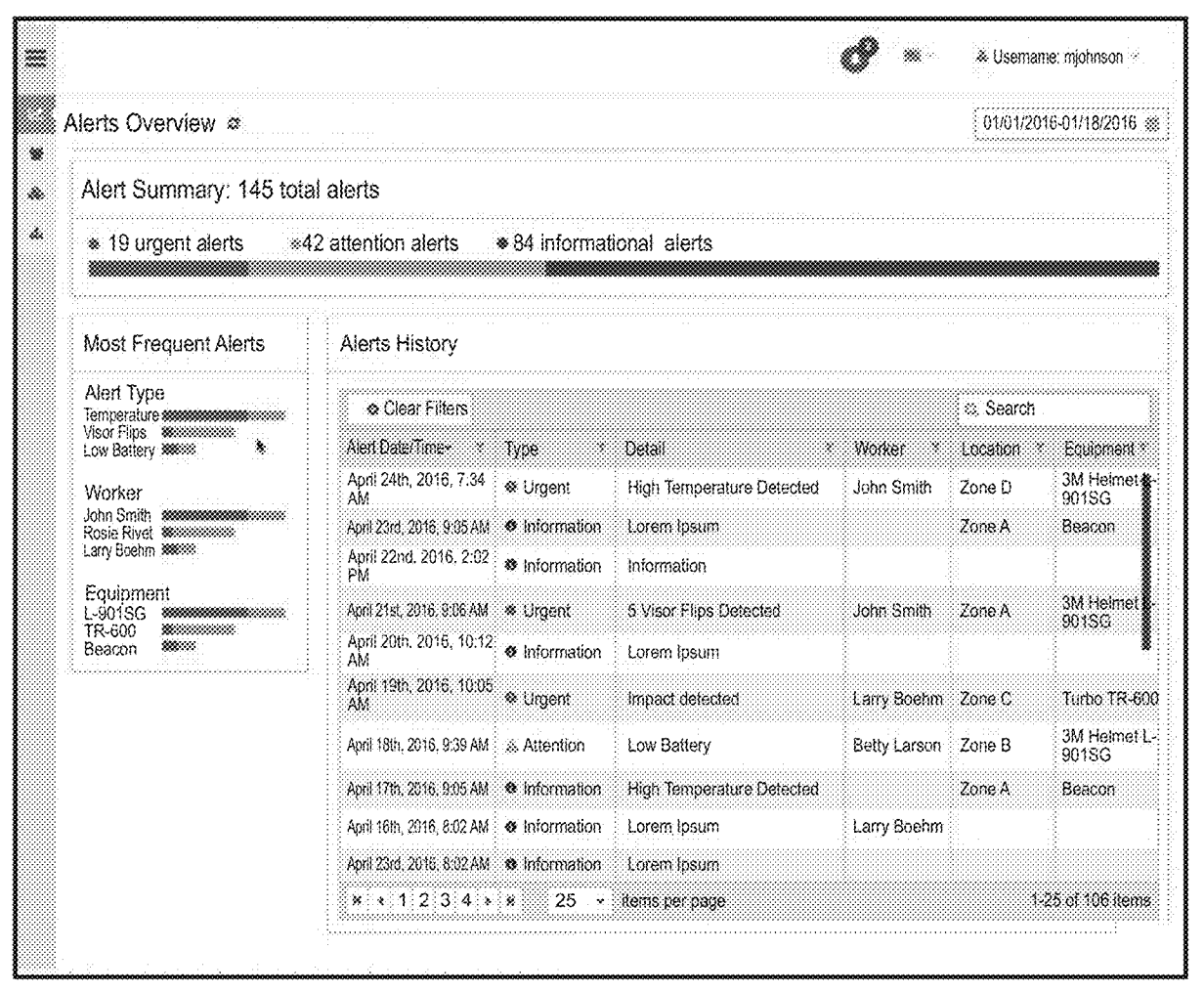
Figure 12:
Figure 13:
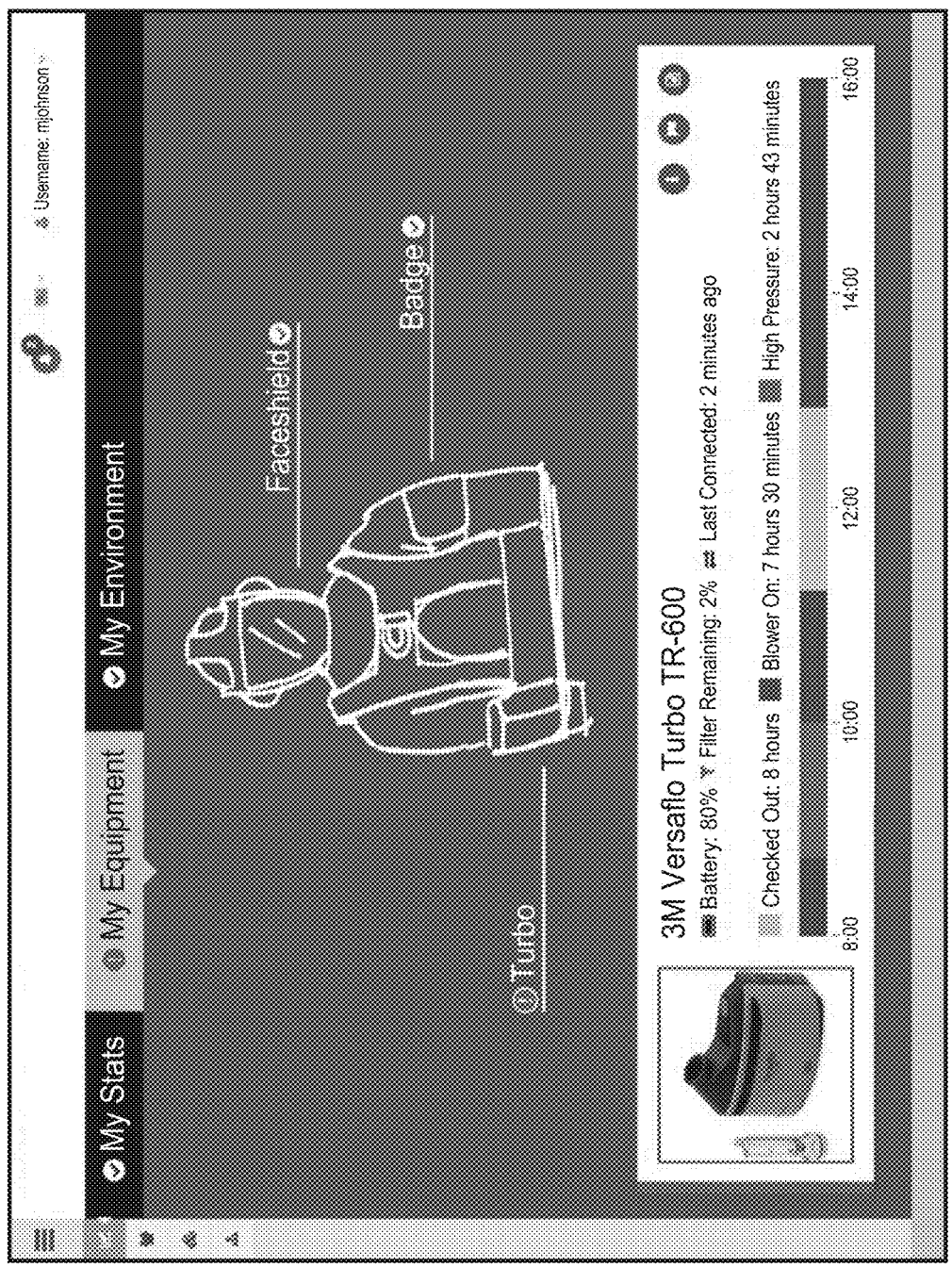

The UIs shown in FIGS. 10-13 may provide various insights regarding system 2, such as baseline ("normal") operation or states across worker populations, identifications of any anomalous workers engaging in abnormal activities that may potentially expose the worker to risks, identifications of any geographic regions within environments 2 for which unusually anomalous (e.g., high) safety events have been or are predicted to occur, identifications of any of environments 8 exhibiting anomalous occurrences of safety events relative to other environments, and the like. For instance, FIG. 10 illustrates user interface controls that indicate "1 urgent condition", "2 attention conditions" and "26 good conditions", each user interface control being selectable to generate more detailed information. FIG. 11 indicates different types of safety events which may correspond to safety event signatures that have been identified based on streams of usage data. For instance, a user interface control is output for display indicating a "high temperature detected" safety event for worker "John Smith" may be detected from a stream of usage data on Apr. 24, 2016 that corresponds to a safety event signature for the "high temperature detected" safety event. In some examples, the user interface control may be selectable to generate more detailed information. FIG. 12 indicates a safety event that worker "Joe Larson" has more visor flips than a threshold (">5 Visor Flip") which may be detected as a number of events in a defined time duration for a stream of usage data. The UI in FIG. 12 may be automatically generated in response to identifying the safety event signature based on a stream of usage data for Joe Larson, such that the UI includes a "Current Status" user interface control with information that is specifically tailored to the worker and/or worker environment for which the safety event occurred. Similarly, the UI may also include Equipment (or PPE) information, Alert History, and/or Worker Information that is specifically tailored to the worker and/or worker environment for which the safety event occurred. FIG. 13 illustrates a time series of usage data for a particular article of PPE in a set of PPE assigned to a worker. In the example of FIG. 13, a safety event is indicated by the "!" icon and further information characterizing the article of PPE corresponding to the safety event is included in the UI (e.g., High Pressure, Blower On, Check Out Time, Battery Life, and Filter remaining).

Figure 14:
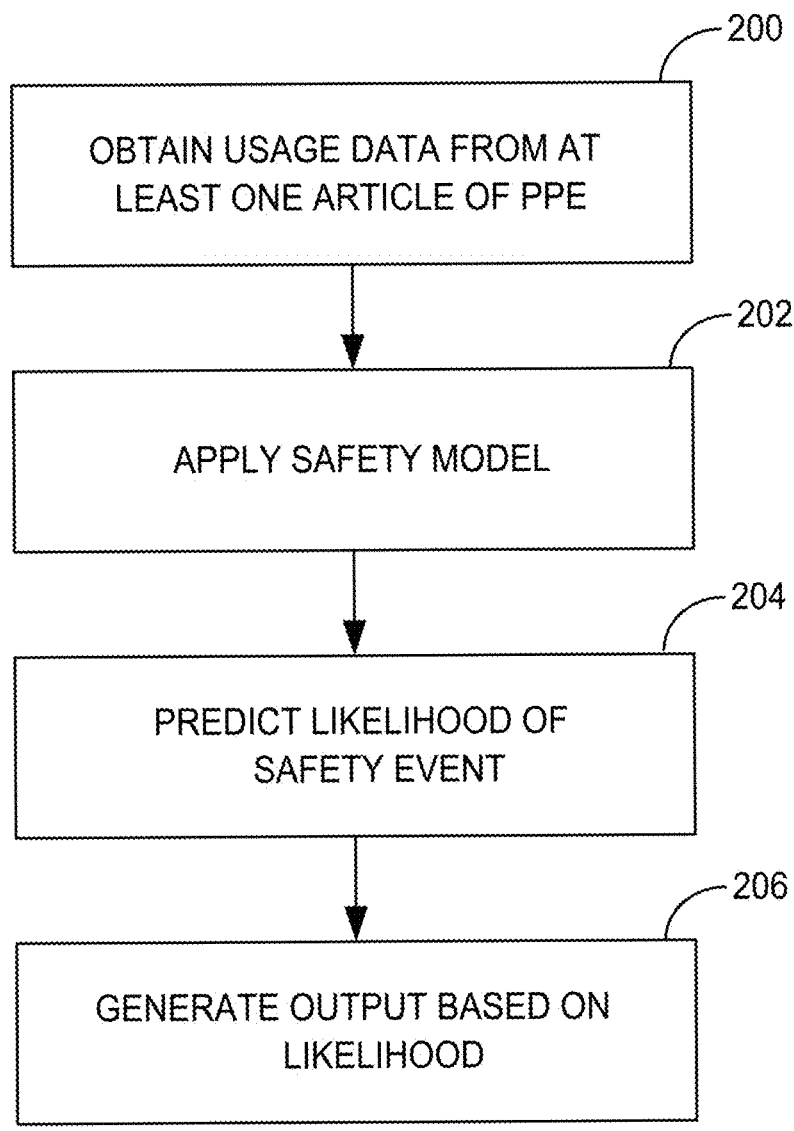
FIG. 14 is a flow diagram illustrating an example process for predicting the likelihood of a safety event, according to aspects of this disclosure.

FIG. 14 is an example process for predicting the likelihood of a safety event, according to aspects of this disclosure. While the techniques shown in FIG. 14 are described with respect to PPEMS 6, it should be understood that the techniques may be performed by a variety of computing devices, such as SRLs 11, respirators 13, head protection 27, and/or hubs 14.

In the illustrated example, PPEMS 6 obtains usage data from at least one article of PPE, such as at least one of PPE 62 (2000). As described herein, the usage data comprises data indicative of operation of PPE 62. In some examples, PPEMS 6 may obtain the usage data by polling PPE 62 or hubs 14 for the usage data. In other examples, PPE 62 or hubs 14 may send usage data to PPEMS 6. For example, PPEMS 6 may receive the usage data from PPE 62 or hubs 14 in real time as the usage data is generated. In other examples, PPEMS 6 may receive stored usage data.

PPEMS 6 may apply the usage data to a safety model that characterizes activity of a user of the at least one PPE 62 (2002). For example, as described herein, the safety model may be trained based on data from known safety events and/or historical data from PPE 62. In this way, the safety model may be arranged to define safe regions and regions unsafe.

PPEMS 6 may predict a likelihood of an occurrence of a safety event associated with the at least one PPE 62 based on application of the usage data to the safety model, where the safety event corresponds to or is mapped to a safety event signature associated with a value representing the likelihood (2004). For example, PPEMS 6 may apply the obtained usage data to the safety model to determine whether the usage data is consistent with safe activity (e.g., as defined by the model) or potentially unsafe activity.

PPEMS 6 may generate an output in response to predicting the likelihood of the occurrence of the safety event (2006). For example, PPEMS 6 may generate alert data when the usage data is not consistent with safe activity (as defined by the safety model). PPEMS 6 may send the alert data to PPE 62, a safety manager, or another third party that indicates the likelihood of the occurrence of the safety event.

Example 1

A method comprising: obtaining usage data from at least one article of personal protective equipment (PPE), wherein the usage data comprises data indicative of operation of the at least one article of PPE; applying, by an analytics engine, the usage data to a safety model that characterizes activity of a user of the at least one article of PPE; predicting a likelihood of an occurrence of a safety condition associated with the at least one article of PPE based on application of the usage data to the safety model; and generating an output in response to predicting the likelihood of the occurrence of the safety event.

Example 2

The method of Example 1, wherein the safety model is constructed from historical data of known safety events from a plurality of air respirator systems having similar characteristics to the at least one article of PPE.

Example 3

The method of any of Examples 1-2, further comprising updating the safety model based on the usage data from the at least one article of PPE.

Example 4

The method of any of Examples 1-3, further comprising selecting the safety model based on at least one of a configuration of the at least one article of PPE, a user of the at least one article of PPE, an environment in which the at least one article of PPE is located, or one or more other devices that are in use with the at least one article of PPE.

Example 5

The method of any of Examples 1-4, wherein the usage data comprises environmental data associated with an environment in which the at least article of PPE is located, such that the likelihood of the occurrence of the safety event is based on the environment in which the at least one article of PPE is located.

Example 6

The method of any of Examples 1-5, wherein applying the usage data to the safety model that characterizes activity of the user comprises applying the usage data to a safety model that is constructed from training data of know safety events associated with a plurality of PPE.

Example 7

The method of any of examples 1-6, wherein predicting the likelihood of the occurrence of the safety event comprises identifying anomalous behavior of a user of the at least one PPE relative to known safe behavior characterized by the safety model.

Example 8

The method of any of Examples 1-7, wherein predicting the likelihood of the occurrence of the safety event further comprises identifying regions within a work environment in which the at least one PPE is deployed that are associated with an anomalous number of safety events.

Example 9

The method of any of Examples 1-8, wherein applying the usage data to the safety model comprises applying the usage data to a safety model that characterizes a motion of a user of at least one PPE, and wherein predicting the likelihood of the occurrence of the safety event comprises determining that the motion of the user over a time period is anomalous for a user of the at least one PPE.

Example 10

The method of any of Examples 1-9, wherein applying the usage data to the safety model comprises applying the usage data to a safety model that characterizes a temperature of the user, and wherein predicting the likelihood of the occurrence of the safety event comprises determining that the temperature exceeds a temperature associated with safe activity over the time period.

Example 11

The method of any of Examples 1-10, wherein generating the output comprises generating alert data that indicates that a safety event is likely.

Example 12

The method of any of Examples 1-11, wherein the method is performed by one or more of an article of PPE, a worker device, a computing device, or at least one server.

Example 13

A computing device comprising: a memory; and one or more computer processors that perform any of the method of Examples 1-12.

Example 14

An apparatus comprising means for performing any of the method of Examples 1-13.

Example 15

A non-transitory computer-readable storage medium encoded with instructions that, when executed, cause at least one processor of a computing device to perform any of the method of claims 1-12.

Example 16

A method comprising receiving, with a communication component, a stream of usage data from the at least one sensor of an article of PPE, wherein the article of PPE has at least one sensor configured to generate the stream of usage data; storing at least a portion of the stream of usage data and at least one model for detecting a safety event signature, wherein the at least one model is trained based as least in part on a set of usage data generated, prior to receiving the stream of usage data, by one or more other articles of PPE of a same type as the article of PPE; detecting, with an analytical stream processing component, the safety event signature in the stream of usage data based on processing the stream of usage data with the model; and generating an output in response to detecting the safety event signature.

Example 17

The method of Example 16, further comprising selecting a training set comprising a set of training instances, each training instance comprising an association between usage data over a defined time duration and a safety event, wherein the usage data comprise one or more metrics that characterize at least one of a user, a work environment, or one or more articles of PPE; and for each training instance in the training set, modifying, based on particular usage data over the defined time duration and a particular safety event of the training instance, the model to change a likelihood predicted by the model for the particular safety event signature associated with the safety event in response to subsequent usage data over the defined time duration applied to the model.

Example 18

The method of any of Examples 16-17, wherein one or more training instances of the set of training instances are generated from use of one or more articles of PPE after the one or more computer processors detect the safety event signature.

Example 19

The method of any of Examples 16-18, wherein the safety event signature comprises at least one of an anomaly in a set of usage data, a pattern in a set of usage data, a particular set of occurrences of particular events over a defined period of time, a particular set of types of particular events over a defined period of time, a particular set of magnitudes of particular events over a defined period of time, a value that satisfies a threshold.

Example 20

The method of any of Examples 16-19, wherein the safety event signature is mapped to a safety event, wherein the safety event is associated with at least one of a worker, the article of PPE, an article of PPE other than the article of PPE, or a work environment.

Example 21

The method of any of Examples 16-20, wherein the safety event comprises at least one of an abnormal condition of worker behavior, an abnormal condition of the article of PPE, an abnormal condition in the work environment, or a violation of a safety regulation.

Example 22

The method of any of Examples 16-21, further comprising prior to detecting the safety event signature, determine, based at least in part on the data stream of usage data, that the article of PPE is operating in a normal state; and in response to detecting the safety event signature, determining that the article of PPE is not operating in the normal state.

Example 23

The method of any of Examples 16-22, wherein the portion of the stream of usage data is a first portion of the stream of usage data, wherein the safety event signature is a first safety event signature, wherein the normal state corresponds to a second safety event signature, wherein the first portion of the data stream corresponds to the first safety event signature, and wherein a second portion of the data stream corresponds to the second safety event signature.

Example 24

The method of any of Examples 16-23, wherein at least one of the analytical stream processing component or the communication component is included in the article of PPE.

Example 25

The method of any of Examples 16-24, wherein at least one of the analytical stream processing component or the communication component is included in a worker device assigned a particular worker, wherein the article of PPE is assigned to the particular worker.

Example 26

The method of any of Examples 16-25, wherein at least one of the analytical stream processing component or the communication component is included in a computing device positioned at a location within a work environment in which a worker operates, wherein the article of PPE is assigned to the worker.

Example 27

The method of any of Examples 16-26, wherein the communication component is included in the article of PPE, a worker device assigned to a particular worker, or a computing device positioned at a location within a work environment, an at least one server is configured to receive the stream of usage data, store the at least one model, and detect the safety event signature in the stream of usage data based on processing the stream of usage data with the model.

Example 28

The method of any of Examples 16-27, further comprising selecting at least one of the article of PPE, the worker device, the computing device, or the at least one server to detect the safety event signature in the stream of usage data.

Example 29

The method of any of Examples 16-28, wherein the selecting occurs at the at least one of article of PPE, the worker device, the computing device, or the at least one server to detect the safety event signature in the stream of usage data.

Example 30

The method of any of Examples 16-29 further comprising selecting based on a power consumption associated with detecting the safety event signature, a latency associated with detecting the safety event signature, a connectivity status of the article of PPE, the worker device, the computing device, or the at least one server, a data type of the usage data, a data volume of the usage data, and the content of the usage data.

Example 31

The method of any of Examples 16-30, wherein at least one sensor generates usage data that characterizes at least a worker associated with the article of PPE or a work environment and wherein detecting the safety event signature in the stream of usage comprises processing the usage data that characterizes the worker associated with the article of PPE or the work environment.

Example 32

The method of any of Examples 16-31, wherein generating the output in response to detecting the safety event signature, comprises sending a notification to at least one of the article of PPE, a hub associated with a user and configured to communicate with the article of PPE and at least one remote computing device, or a computing device associated with person who is not the user.

Example 33

The method of any of Examples 16-32, wherein generating the output in response to detecting the safety event signature, comprises sending a notification that alters an operation of the article of PPE.

Example 34

The method of any of Examples 16-33, wherein generating the output in response to detecting the safety event signature comprises outputting for display a user interface that indicates the safety event in association with at least one of a user, work environment, or the article of PPE.

Example 35

The method of any of Examples 16-34, wherein the article of PPE comprises at least one of an air respirator system, a fall protection device, a hearing protector, a head protector, a garment, a face protector, an eye protector, a welding mask, or an exosuit.

Example 36

The method of any of Examples 16-35, wherein the article of PPE is included in a set of articles of PPE associated with a user, wherein each article of PPE in the set of articles of PPE includes a motion sensor, wherein the one or more computer processors: receive a respective stream of usage data from each respective motion sensor of each respective article of PPE of the set of articles of PPE; and to detect the safety event signature, the one or more computer processors detect the safety event signature corresponding to a relative motion that is based at least in part on the respective stream of usage data from each respective motion sensor.

Example 37

The method of any of Examples 16-36, wherein the stream of usage data comprises events, wherein each respective event is generated at a same defined interval, wherein each respective event includes a respective set of values that correspond to a same set of defined metrics, and wherein respective sets of values in different respective events are different.

Example 38

The method of any of Examples 16-37, wherein the set of defined metrics comprises one or more of a timestamp, characteristics of the article of PPE, characteristics of a worker associated with the article of PPE, or characteristics a work environment.

Example 39

The method of any of Examples 16-38, wherein at least one safety rule is mapped to at least one safety event, wherein the at least one safety event is mapped to the safety event signature, and wherein the safety event signature corresponds to at least the portion of the stream of usage data.

Example 40

The method of any of Examples 16-39, wherein detecting the safety event signature in the stream of usage data based on processing the stream of usage data with the model comprises determining a set of one or more likelihoods associated with one or more safety event signatures, wherein the safety event signature is associated with a likelihood in the set of one or more likelihoods associated with one or more safety event signatures.

Example 41

The method of any of Examples 16-40, wherein generating an output in response to detecting the safety event signature comprises generating a user interface that is based at least in part on a safety event that corresponds to the safety event signature.

Example 42

The method of any of Examples 16-41, wherein user interface includes at least one input control that requires a responsive user input within a threshold time period, the method further comprising in response to the threshold time period expiring without the responsive user input, perform at least one operation based at least in part on the threshold time period expiring without the responsive user input.

Example 43

The method of any of Examples 16-42, wherein the safety event signature corresponds to a safety event that indicates ergonomic stress that satisfies a threshold.

Example 44

A computing device comprising: a memory; and one or more computer processors that perform any of the method of Examples 16-43.

Example 45

An apparatus comprising means for performing any of the method of Examples 16-43.

Example 46

A non-transitory computer-readable storage medium encoded with instructions that, when executed, cause at least one processor of a computing device to perform any of the method of claims 16-43.

Example 47

A method comprising: receiving one or more streams of usage data from a set of sensors that generate the one or more streams of usage data corresponding to at least one of an article of PPE, a worker, or a work environment; storing at least a portion of the one or more streams of usage data and at least one model for detecting a safety event signature, wherein the at least one model is trained based as least in part on a set of usage data generated, prior to receiving the one or more streams of usage data, by one or more other articles of PPE, workers, or work environments of a same type as the at least one of the article of PPE, the worker, or the work environment; detecting the safety event signature in the one or more streams of usage data based on processing the one or more streams of usage data with the model, and generating an output in response to detecting the safety event signature.

Example 48

The method of Example 47 further comprising the method of any of claims 16-43.

Example 49

A computing device comprising: a memory; and one or more computer processors that perform any of the method of Example 48.

Example 50

An apparatus comprising means for performing any of the method of Example 48.

Example 51

A non-transitory computer-readable storage medium encoded with instructions that, when executed, cause at least one processor of a computing device to perform any of the method of Example 48.

It is to be recognized that depending on the example, certain acts or events of any of the techniques described herein can be performed in a different sequence, may be added, merged, or left out altogether (e.g., not all described acts or events are necessary for the practice of the techniques). Moreover, in certain examples, acts or events may be performed concurrently, e.g., through multi-threaded processing, interrupt processing, or multiple processors, rather than sequentially.

In one or more examples, the functions described may be implemented in hardware, software, firmware, or any combination thereof. If implemented in software, the functions may be stored on or transmitted over a computer-readable medium as one or more instructions or code, and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transitory media, but are instead directed to non-transitory, tangible storage media. Disk and disc, as used herein, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Instructions may be executed by one or more processors, such as one or more digital signal processors (DSPs), general purpose microprocessors, application specific integrated circuits (ASICs), field programmable gate arrays (FPGAs), or other equivalent integrated or discrete logic circuitry, as well as any combination of such components. Accordingly, the term "processor," as used herein may refer to any of the foregoing structures or any other structure suitable for implementation of the techniques described herein. In addition, in some aspects, the functionality described herein may be provided within dedicated hardware and/or software modules. Also, the techniques could be fully implemented in one or more circuits or logic elements.

The techniques of this disclosure may be implemented in a wide variety of devices or apparatuses, including a wireless communication device or wireless handset, a microprocessor, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

Various examples have been described. These and other examples are within the scope of the following claims.

What is claimed is:

1. A system comprising:
   an article of personal protective equipment (PPE) having at least one sensor configured to generate a stream of usage data; and
   an analytical stream processing component comprising:
      a communication component that receives the stream of usage data from the at least one sensor of the article of PPE;
      a memory configured to store at least a portion of the stream of usage data and at least one model for detecting a safety event signature indicative of a predicted occurrence of an imminent safety event, wherein the at least one model is trained based at least in part on a set of usage data generated, prior to receiving the stream of usage data, by one or more other articles of PPE of a same type as the article of PPE; and
      one or more computer processors configured to:
         detect the safety event signature indicative of the predicted occurrence of the imminent safety event in the stream of usage data based on processing the stream of usage data with the model, and
         generate an output in response to detecting the safety event signature.

2. The system of claim 1, wherein the one or more computer processors:
   select a training set comprising a set of training instances, each training instance comprising an association between usage data over a defined time duration and a safety event, wherein the usage data comprise one or more metrics that characterize at least one of a user, a work environment, or one or more articles of PPE; and for each training instance in the training set, modify, based on particular usage data over the defined time duration and a particular safety event of the training instance, the model to change a likelihood predicted by the model for the particular safety event signature associated with the safety event in response to subsequent usage data over the defined time duration applied to the model.

3. The system of claim 2, wherein one or more training instances of the set of training instances are generated from use of one or more articles of PPE after the one or more computer processors detect the safety event signature.

4. The system of claim 1, wherein the safety event signature comprises at least one of an anomaly in a set of usage data, a pattern in a set of usage data, a particular set of occurrences of particular events over a defined period of time, a particular set of types of particular events over a defined period of time, a particular set of magnitudes of particular events over a defined period of time, a value that satisfies a threshold.

5. The system of claim 1, wherein the safety event signature is mapped to a safety event, wherein the safety event is associated with at least one of a worker, the article of PPE, an article of PPE other than the article of PPE, or a work environment.

6. The system of claim 5, wherein the safety event comprises at least one of an abnormal condition of worker behavior, an abnormal condition of the article of PPE, an abnormal condition in the work environment, or a violation of a safety regulation.

7. The system of claim 1, wherein the one or more computer processors:
   prior to detection of the safety event signature, determine, based at least in part on the data stream of usage data, that the article of PPE is operating in a normal state; and
   in response to detection of the safety event signature, determine that the article of PPE is not operating in the normal state.

8. The system of claim 7,
   wherein the portion of the stream of usage data is a first portion of the stream of usage data,
   wherein the safety event signature is a first safety event signature,
   wherein the normal state corresponds to a second safety event signature indicative of a second predicted occurrence of a second imminent safety event,
   wherein the first portion of the data stream corresponds to the first safety event signature, and
   wherein a second portion of the data stream corresponds to the second safety event signature.

9. The system of claim 1, wherein at least one of the analytical stream processing component or the communication component is included in the article of PPE.

10. The system of claim 1, wherein at least one of the analytical stream processing component or the communication component is included in a worker device assigned a particular worker, wherein the article of PPE is assigned to the particular worker.

11. The system of claim 1, wherein at least one of the analytical stream processing component or the communication component is included in a computing device positioned at a location within a work environment in which a worker operates, wherein the article of PPE is assigned to the worker.

12. The system of claim 1, wherein the communication component is included in the article of PPE, a worker device assigned to a particular worker, or a computing device positioned at a location within a work environment, the system further comprising at least one server configured to receive the stream of usage data, store the at least one model, and detect the safety event signature in the stream of usage data based on processing the stream of usage data with the model.

13. The system of claim 12, further comprising a selection component configured to select at least one of the article of PPE, the worker device, the computing device, or the at least one server to detect the safety event signature in the stream of usage data.

14. The system of claim 13, wherein the selection component is incorporated in at least one of the article of PPE, the worker device, the computing device, or the at least one server to detect the safety event signature in the stream of usage data.

15. The system of claim 13, wherein the selection component is configured to select based on a power consumption associated with detecting the safety event signature, a latency associated with detecting the safety event signature, a connectivity status of the article of PPE, the worker device, the computing device, or the at least one server, a data type of the usage data, a data volume of the usage data, and the content of the usage data.

16. The system of claim 1, further comprising:
   at least one sensor that generates usage data that characterizes at least a worker associated with the article of PPE or a work environment; and
   wherein, to detect the safety event signature in the stream of usage, the one or more computer processors process the usage data that characterizes the worker associated with the article of PPE or the work environment.

17. The system of claim 1, wherein to generate the output in response to detecting the safety event signature, the one or more computer processors send a notification to at least one of the article of PPE, a hub associated with a user and configured to communicate with the article of PPE and at least one remote computing device, or a computing device associated with person who is not the user.

18. The system of claim 1, wherein to generate the output in response to detecting the safety event signature, the one or more computer processors send a notification that alters an operation of the article of PPE.

19. The system of claim 1, wherein to generate the output in response to detecting the safety event signature, the one or more computer processors output for display a user interface that indicates the safety event in association with at least one of a user, work environment, or the article of PPE.

20. The system of claim 1, wherein the article of PPE comprises at least one of an air respirator system, a fall protection device, a hearing protector, a head protector, a garment, a face protector, an eye protector, a welding mask, or an exosuit.

21. The system of claim 1,
   wherein the article of PPE is included in a set of articles of PPE associated with a user,
   wherein each article of PPE in the set of articles of PPE includes a motion sensor,
   wherein the one or more computer processors:

receive a respective stream of usage data from each respective motion sensor of each respective article of PPE of the set of articles of PPE; and to detect the safety event signature, the one or more computer processors detect the safety event signature corresponding to a relative motion that is based at least in part on the respective stream of usage data from each respective motion sensor.

22. The system of claim 1, wherein the stream of usage data comprises events, wherein each respective event is generated at a same defined interval, wherein each respective event includes a respective set of values that correspond to a same set of defined metrics, and wherein respective sets of values in different respective events are different.

23. The system of claim 22, wherein the set of defined metrics comprises one or more of a timestamp, characteristics of the article of PPE, characteristics of a worker associated with the article of PPE, or characteristics a work environment.

24. The system of claim 1, wherein at least one safety rule is mapped to at least one safety event, wherein the at least one safety event is mapped to the safety event signature, and wherein the safety event signature corresponds to at least the portion of the stream of usage data.

25. The system of claim 1, wherein to detect the safety event signature in the stream of usage data based on processing the stream of usage data with the model the one or more computer processors determine a set of one or more likelihoods associated with one or more safety event signatures, wherein the safety event signature is associated with a likelihood in the set of one or more likelihoods associated with one or more safety event signatures.

26. The system of claim 1, wherein to generate an output in response to detecting the safety event signature, the one or more processors generate a user interface that is based at least in part on a safety event that corresponds to the safety event signature.

27. The system of claim 26, wherein the user interface includes at least one input control that requires a responsive user input within a threshold time period, wherein the one or more computer processors:

in response to the threshold time period expiring without the responsive user input, perform at least one operation based at least in part on the threshold time period expiring without the responsive user input.

28. The system of claim 1, wherein the safety event signature corresponds to a safety event that indicates ergonomic stress that satisfies a threshold.

29. A computing device comprising:

one or more computer processors that receive a stream of usage data from at least one sensor of an article of personal protective equipment (PPE), wherein the article of PPE has the at least one sensor configured to generate the stream of usage data;

a memory that stores at least a portion of the stream of usage data and at least one model for detecting a safety event signature indicative of a predicted occurrence of an imminent safety event, wherein the at least one model is trained based at least in part on a set of usage data generated, prior to receiving the stream of usage data, by one or more other articles of PPE of a same type as the article of PPE;

wherein the one or more computer processors detect the safety event signature indicative of the predicted occurrence of the imminent safety event in the stream of usage data based on processing the stream of usage data with the model; and wherein the one or more computer processors generate an output in response to detecting the safety event signature.

30. The computing device of claim 29, wherein the one or more computer processors:

select a training set comprising a set of training instances, each training instance comprising an association between usage data over a defined time duration and a safety event, wherein the usage data comprise one or more metrics that characterize at least one of a user, a work environment, or one or more articles of PPE; and for each training instance in the training set, modify, based on particular usage data over the defined time duration and a particular safety event of the training instance, the model to change a likelihood predicted by the model for the particular safety event signature associated with the safety event in response to subsequent usage data over the defined time duration applied to the model.

31. The computing device of claim 30, wherein one or more training instances of the set of training instances are generated from use of one or more articles of PPE after the one or more computer processors detect the safety event signature.

32. The computing device of claim 29, wherein the safety event signature comprises at least one of an anomaly in a set of usage data, a pattern in a set of usage data, a particular set of occurrences of particular events over a defined period of time, a particular set of types of particular events over a defined period of time, a particular set of magnitudes of particular events over a defined period of time, a value that satisfies a threshold.

33. The computing device of claim 29, wherein the safety event signature is mapped to a safety event, wherein the safety event is associated with at least one of a worker, the article of PPE, an article of PPE other than the article of PPE, or a work environment.

34. The computing device of claim 33, wherein the safety event comprises at least one of an abnormal condition of worker behavior, an abnormal condition of the article of PPE, an abnormal condition in the work environment, or a violation of a safety regulation.

35. The computing device of claim 29, wherein the one or more computer processors:

prior to detecting the safety event signature, determine, based at least in part on the data stream of usage data, that the article of PPE is operating in a normal state; and in response to detecting the safety event signature, determining that the article of PPE is not operating in the normal state.

36. The computing device of claim 35, wherein the portion of the stream of usage data is a first portion of the stream of usage data, wherein the safety event signature is a first safety event signature, wherein the normal state corresponds to a second safety event signature indicative of a second predicted occurrence of a second imminent safety event, wherein the first portion of the data stream corresponds to the first safety event signature, and wherein a second portion of the data stream corresponds to the second safety event signature.

37. The computing device of claim 29, wherein the computing device is included at the article of PPE.

38. The computing device of claim 29, wherein computing device is included at a worker device assigned a particular worker, wherein the article of PPE is assigned to the particular worker.

39. The computing device of claim 29, wherein the computing device is positioned at a location within a work environment in which a worker operates, wherein the article of PPE is assigned to the worker.

40. The computing device of claim 29, wherein a communication component is communicatively coupled to the computing device, wherein the communication component is included in the article of PPE, a worker device assigned to a particular worker, or a computing device positioned at a location within a work environment, and at least one server is configured to receive the stream of usage data, store the at least one model, and detect the safety event signature in the stream of usage data based on processing the stream of usage data with the model.

41. The computing device of claim 40, wherein the one or more computer processors:
select at least one of the article of PPE, the worker device, the computing device, or the at least one server to detect the safety event signature in the stream of usage data.

42. The computing device of claim 41, wherein the selection occurs at the at least one of the article of PPE, the worker device, the computing device, or the at least one server to detect the safety event signature in the stream of usage data.

43. The computing device of claim 41, wherein the selection is based on a power consumption associated with detecting the safety event signature, a latency associated with detecting the safety event signature, a connectivity status of the article of PPE, the worker device, the computing device, or the at least one server, a data type of the usage data, a data volume of the usage data, and the content of the usage data.

44. The computing device of claim 29, wherein at least one sensor generates usage data that characterizes at least a worker associated with the article of PPE or a work environment and wherein detecting the safety event signature in the stream of usage comprises processing the usage data that characterizes the worker associated with the article of PPE or the work environment.

45. The computing device of claim 29, wherein to generate the output in response to detecting the safety event signature, the one or more computer processors send a notification to at least one of the article of PPE, a hub associated with a user and configured to communicate with the article of PPE and at least one remote computing device, or a computing device associated with person who is not the user.

46. The computing device of claim 29, wherein to generate the output in response to detection of the safety event signature, the one or more computer processors send a notification that alters an operation of the article of PPE.

47. The computing device of claim 29, wherein to generate the output in response to detection of the safety event signature the one or more computer processors output for display a user interface that indicates the safety event in association with at least one of a user, work environment, or the article of PPE.

48. The computing device of claim 29, wherein the article of PPE comprises at least one of an air respirator system, a fall protection device, a hearing protector, a head protector, a garment, a face protector, an eye protector, a welding mask, or an exosuit.

49. The computing device of claim 29, wherein the article of PPE is included in a set of articles of PPE associated with a user, wherein each article of PPE in the set of articles of PPE includes a motion sensor, wherein the one or more computer processors:
receive a respective stream of usage data from each respective motion sensor of each respective article of PPE of the set of articles of PPE; and
to detect the safety event signature, the one or more computer processors detect the safety event signature corresponding to a relative motion that is based at least in part on the respective stream of usage data from each respective motion sensor.

50. The computing device of claim 29, wherein the stream of usage data comprises events, wherein each respective event is generated at a same defined interval, wherein each respective event includes a respective set of values that correspond to a same set of defined metrics, and wherein respective sets of values in different respective events are different.

51. The computing device of claim 50, wherein the set of defined metrics comprises one or more of a timestamp, characteristics of the article of PPE, characteristics of a worker associated with the article of PPE, or characteristics a work environment.

52. The computing device of claim 29, wherein at least one safety rule is mapped to at least one safety event, wherein the at least one safety event is mapped to the safety event signature, and wherein the safety event signature corresponds to at least the portion of the stream of usage data.

53. The computing device of claim 29, wherein to detect the safety event signature in the stream of usage data based on processing the stream of usage data with the model, the one or more computer processors determine a set of one or more likelihoods associated with one or more safety event signatures, wherein the safety event signature is associated with a likelihood in the set of one or more likelihoods associated with one or more safety event signatures.

54. The computing device of claim 29, wherein to generate an output in response to detecting the safety event signature, the one or more processors generate a user interface that is based at least in part on a safety event that corresponds to the safety event signature.

55. The computing device of claim 54, wherein the user interface includes at least one input control that requires a responsive user input within a threshold time period, wherein the one or more computer processors:
in response to the threshold time period expiring without the responsive user input, perform at least one operation based at least in part on the threshold time period expiring without the responsive user input.

56. The computing device of claim 29, wherein the safety event signature corresponds to a safety event that indicates ergonomic stress that satisfies a threshold.

\* \* \* \* \*